(12) United States Patent
Alt et al.

(10) Patent No.: US 11,974,553 B2
(45) Date of Patent: *May 7, 2024

(54) HIGH-THROUGHPUT MOUSE MODEL FOR OPTIMIZING ANTIBODY AFFINITIES

(71) Applicant: CHILDREN'S MEDICAL CENTER CORPORATION, Boston, MA (US)

(72) Inventors: Frederick W. Alt, Cambridge, MA (US); Hwei-Ling Cheng, Northborough, MA (US); Ming Tian, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 1531 days.

This patent is subject to a terminal disclaimer.

(21) Appl. No.: 16/017,221

(22) Filed: Jun. 25, 2018

(65) Prior Publication Data

US 2018/0295822 A1    Oct. 18, 2018

Related U.S. Application Data

(63) Continuation of application No. 15/112,557, filed as application No. PCT/US2015/012577 on Jan. 23, 2015, now Pat. No. 10,034,463.

(60) Provisional application No. 61/931,074, filed on Jan. 24, 2014.

(51) Int. Cl.
| | |
|---|---|
| *A01K 67/0278* | (2024.01) |
| *A01K 67/0271* | (2024.01) |
| *C07K 16/00* | (2006.01) |
| *C07K 16/10* | (2006.01) |
| *C12N 15/85* | (2006.01) |

(52) U.S. Cl.
CPC ...... *A01K 67/0278* (2013.01); *A01K 67/0271* (2013.01); *C07K 16/00* (2013.01); *C07K 16/1045* (2013.01); *C12N 15/8509* (2013.01); *A01K 2207/12* (2013.01); *A01K 2207/15* (2013.01); *A01K 2217/052* (2013.01); *A01K 2217/054* (2013.01); *A01K 2217/072* (2013.01); *A01K 2217/15* (2013.01); *A01K 2227/105* (2013.01); *A01K 2267/01* (2013.01); *A01K 2267/03* (2013.01); *C07K 2317/14* (2013.01); *C07K 2317/21* (2013.01); *C07K 2317/24* (2013.01); *C07K 2317/51* (2013.01); *C07K 2317/56* (2013.01); *C07K 2317/76* (2013.01); *C07K 2317/92* (2013.01); *C12N 2015/8518* (2013.01); *C12N 2015/8527* (2013.01); *C12N 2800/30* (2013.01)

(58) Field of Classification Search
CPC ............ A01K 67/0278; A01K 67/0271; A01K 2207/12; A01K 2207/15; A01K 2217/052; A01K 2217/054; A01K 2217/072; A01K 2217/15; A01K 2227/105; A01K 2267/01; A01K 2267/03; C07K 16/00; C07K 16/1045; C07K 2317/14; C07K 2317/21; C07K 2317/24; C07K 2317/51; C07K 2317/56; C07K 2317/76; C07K 2317/92; C12N 15/8509; C12N 2015/8518; C12N 2015/8527; C12N 2800/30

See application file for complete search history.

(56) References Cited

U.S. PATENT DOCUMENTS

| | | | |
|---|---|---|---|
| 10,034,463 B2 * | 7/2018 | Alt ................. | C07K 16/00 |
| 2003/0013157 A1 | 1/2003 | Jakobovits et al. | |
| 2011/0123527 A1 | 5/2011 | Shizuya et al. | |
| 2011/0314563 A1 | 12/2011 | Craig | |
| 2013/0096287 A1 | 4/2013 | MacDonald et al. | |

FOREIGN PATENT DOCUMENTS

| | | |
|---|---|---|
| AU | 2013/204582 A1 | 1/2014 |
| WO | 2013/022782 A1 | 2/2013 |
| WO | 2013/041844 A2 | 3/2013 |
| WO | 2013/041846 A2 | 3/2013 |
| WO | 2013/041846 A3 | 3/2013 |
| WO | 2013/059230 A1 | 4/2013 |

OTHER PUBLICATIONS

Shirasawa et al., "The Limitation of u Chain Diversity Generated in Progenies Derived from a Single Precursor Pre-B Cell." Chiba Medical Journal 66:183-191 (1990) (Original English summary available on p. 8).
Guo et al., "CTCF-binding elements mediate control of V(D)J recombination", Nature, 477(7365):424-431, (2011).
Koralav et al., "Antibody repertoires generated by VH replacemetn and direct VH to JH joining", Immunity, 25 (1):43-3 (2006).
Melcher et al., "'Repertoire selection by pre-B-cell receptors and B-cell receptors, and genetic control of B-cell development from immature to mature B cells'", Immunol Rev., 175:33-46 (2000).
Butler et al. "The swine Ig heavy chain locus has a single JH and no identifiable IgD" Int Immunol. 8(12): 1897-904 (1996) 1897-904 (1996).
Denger et al. "Cutting edge: developmental stage-specific recruitment of cohesin to CTCF sites throughout immunoglobulin loci during B lymphocyte development" J Immunol 182(1): 44-48 (2009).
Gambon-Deza et al. "The immunoglobulin heavy chain locus in the platypus (*Ornithorhynchus anatinus*)" Mol Immunol. 46(13):2515-2523 (2009).
Holwerda et al. "Allelic exclusion of the immunoglobulin heavy chain locus is independent of its nuclear localization in mature B cells" Nucleic Acids Res. 41(14):6905-16. (2013).

(Continued)

*Primary Examiner* — Arthur S Leonard
*Assistant Examiner* — Masudur Rahman
(74) *Attorney, Agent, or Firm* — NIXON PEABODY LLP; David S. Resnick; Nicole D. Kling

(57) ABSTRACT

Described herein are compositions (e.g. cells and transgenic animals) and methods relating to engineered Ig loci that permit expression of particular antibodies or antibody segments while still permitting recombination and/or maturation process for antibody optimization.

22 Claims, 6 Drawing Sheets

Specification includes a Sequence Listing.

(56) References Cited

OTHER PUBLICATIONS

Rakhmanov et al. "Analysis of B lymphocyte activation and differentiation by expression profiling" [Doctoral dissertation, Albewrt Ludwigs University]. 2005 May. Accessed from ResearchGate at www.researchgate.net/publication/29756778 (2005).
Xiang et al. "A multifunctional element in the mouse Igk locus that specifies repertoire and Ig loci subnuclear location" JXImmunol. 186(9):5356-66 (2011).

\* cited by examiner

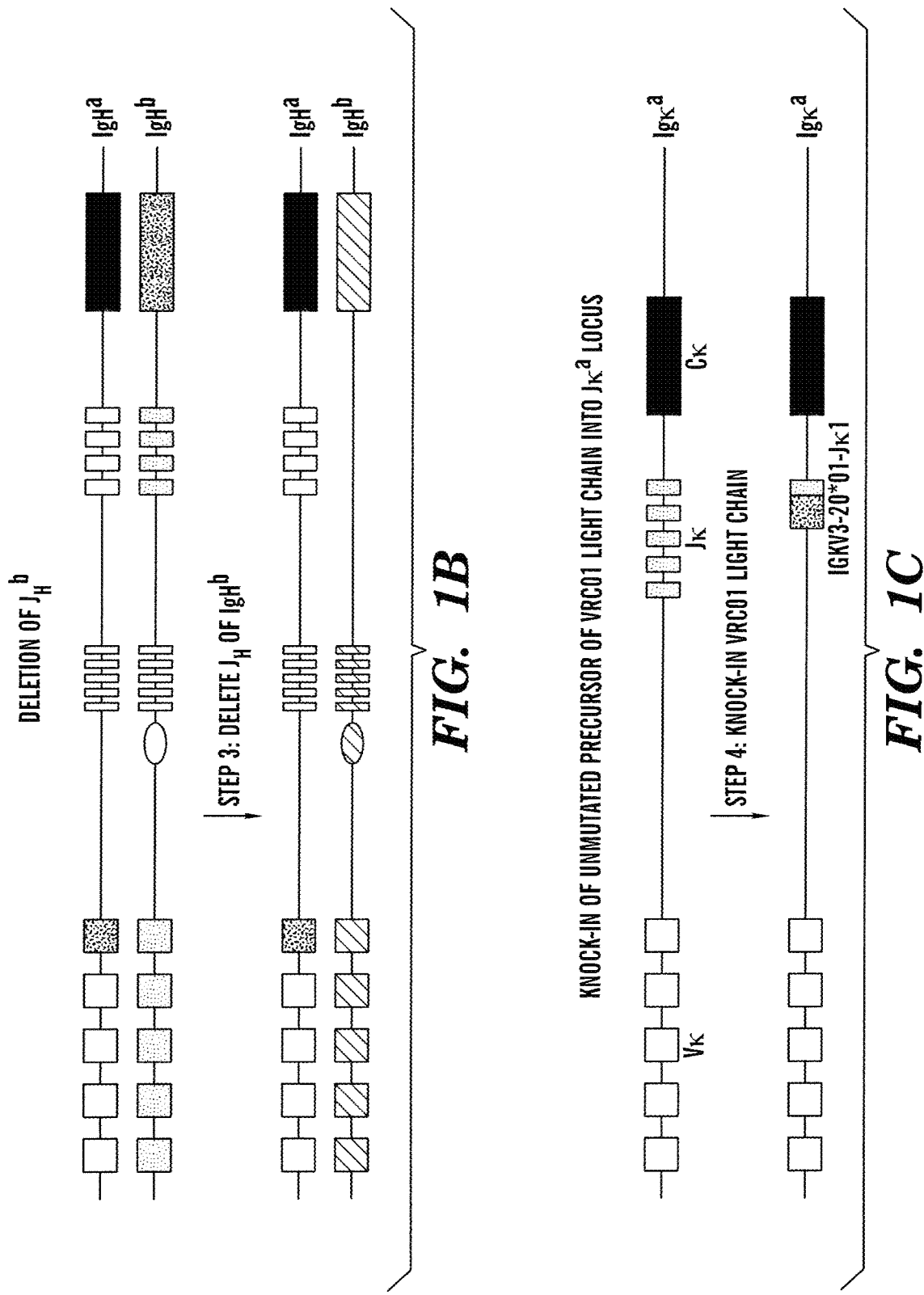

REPRESENTATIVE RESULTS OF PCR AMPLIFICATION OF IGHV1-2*02 REARRANGEMENTS FROM HYBRIDOMAS

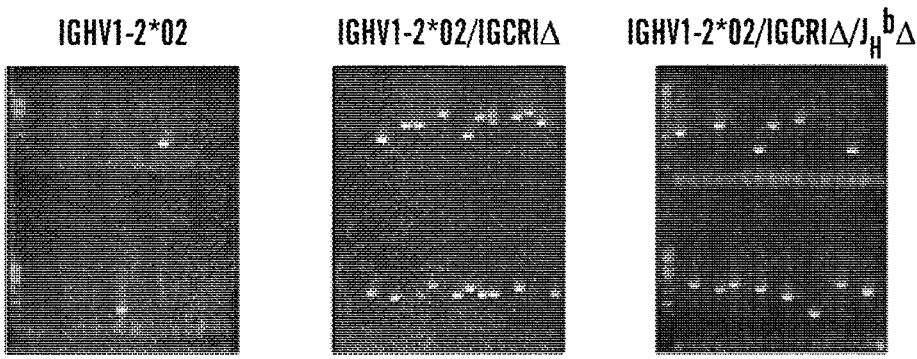

FIG. 2B

FREQUENCY OF IGHV1-2*02 REARRANGEMENTS IN HYBRIDOMAS

|  | IGHV1-2*02 | IGHV1-2*02/IGCRI$\Delta$ | IGHV1-2*02/IGCRI$\Delta$/$J_H^b\Delta$ |
|---|---|---|---|
| IGHV1-2*02$^+$ | 11 | 122 | 65 |
| TOTAL | 303 | 208 | 192 |
| IGHV1-2*02$^+$% | 4% | 59% | 34% |

FIG. 2C

RATIO OF PRODUCTIVE VERSUS NONPRODUCTIVE IGHV1-2*02 REARRANGEMENTS

▨ PRODUCTIVE
☐ NONPRODUCTIVE

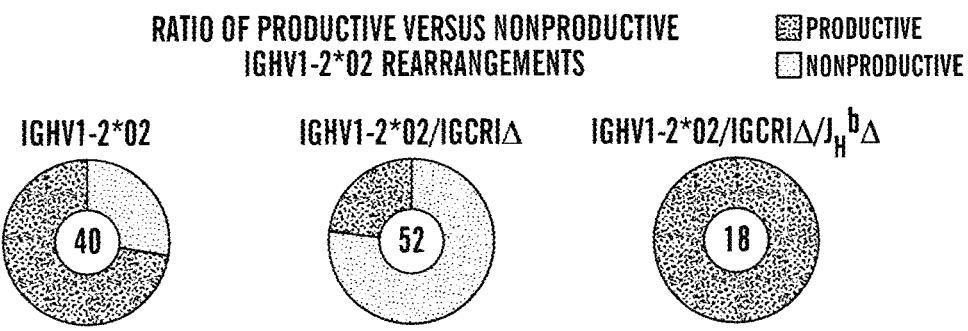

THE NUMBER AT THE CENTER OF PIE CHARTS INDICATES THE TOTAL NUMBER OF SEQUENCED JUNCTIONS; THE DATA FOR IGHV1-2*02 WERE OBTAINED FROM ANALYSIS OF PERIPHERAL BLOOD, WHEREAS THE DATA FOR IGHV1-2*02/IGCRI$\Delta$ AND IGHV1-2*02/IGCRI$\Delta$/$J_H^b\Delta$ WERE BASED ON ANALYSIS OF HYBRIDOMAS.

FIG. 2D

HIGH-THROUGHPUT MOUSE MODEL FOR OPTIMIZING ANTIBODY AFFINITIES

CROSS-REFERENCE TO RELATED APPLICATIONS

This application is a continuation under 35 U.S.C. § 120 of co-pending U.S. application Ser. No. 15/112,557 filed Jul. 19, 2016, which is a 35 U.S.C. § 371 National Phase Entry Application of International Application No. PCT/US2015/012577 filed Jan. 23, 2015, which designates the U.S. and claims benefit under 35 U.S.C. § 119(e) of U.S. Provisional Application No. 61/931,074 filed Jan. 24, 2014, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 13, 2015, is named 701039-080511-PCT_SL.txt and is 1,362 bytes in size.

FIELD OF THE INVENTION

The invention relates to engineered antibodies and methods of generating antibodies and/or identifying antigens.

BACKGROUND

The mammalian adaptive immune response relies upon antibodies. A healthy animal will produce a very large number of different antibodies, each of which can selectively bind to a different molecule, which is called an antigen. The binding of the antibody to an antigen triggers an immune response which allows the body to destroy the antigen. If the antigen is a molecule on a pathogen, this permits the body to counter the infection by attacking the pathogen.

Antibodies are comprised of two identical Ig heavy chain (IgH) polypeptides and two identical light chain (IgL) polypeptides. Portions of the IgH and IgL chains called the variable region form the antigen-binding site. The sequence of the antigen-binding site determines what antigen(s) the antibody can bind to and how tight that binding is. In order to have a robust immune response, it is important for an animal to have both a wide-variety of antigen-binding sites represented in the antibody population so that the body can recognize any given antigen, and a mechanism for improving upon existing antibodies in order to improve the ability to recognize any given antigen.

The IgH variable regions are assembled in the genome of B cells from gene segments referred to as $V_H$, D, and $J_H$. Counting only the functional gene segments, there are 39 $V_H$, 25 D and 6 $J_H$ segments in the human IgH locus. Prior to an antibody being expressed, the IgH gene will be subjected to a process called V(D)J recombination, in which 1 $V_H$, 1 D, and 1 $J_H$ segment are randomly combined in order to create a nucleic acid sequence that encodes a mature antibody. The different combinations of $V_H$, D, and $J_H$, as well as the way the edges of the $V_H$, D, and $J_H$ segments are joined to each other contribute to the extensive diversity of antibodies present in an individual. The light chain present in the B cell will be undergoing a similar set of processes, and further diversity is generated by the pairing of unique light and heavy chains.

If an antibody encounters a foreign antigen to which it can bind, the B cell which makes that particular antibody will be activated. This will cause the B cell to replicate and those resulting B cells can be subject to additional genomic alterations that can lead to further diversification/affinity maturation (e.g. via somatic hypermutation (SHM) or germinal center reaction (GC)) of their antibodies. The efficacy of an antibody depends upon its specificity and affinity toward a relevant antigen. As described above, both V(D)J recombination and SHM make important contributions in this respect but at different points in the evolution of the antibody. V(D)J recombination creates an enormous pool of antigen-binding sites so that any potential antigen might find a reasonable match; once a matched B cell has been found, somatic hypermutation and the GC response fine-tune the antigen-binding site to perfect the antibody-antigen interaction.

By studying natural immune responses, it is possible to identify V, D, and/or J segments that are likely to be involved in generating an immune response to a particular antigen. However, current methods of antibody production do not allow the power of V(D)J recombination, SHM, and GC processes (Lonberg, Nature Biotechnology 23, 1117 (2005)) to be applied to the optimization of existing antibodies.

SUMMARY OF THE INVENTION

The invention relates to, at least in part, a novel and simple method of producing optimized antibodies, using a novel engineered immune system. The engineered immune system is modified to allow easy insertion of one or more non-native components into the Ig locus of a model cell of a model animal. The engineered immune system is modified to drive production of V(D)J recombinations with any desired component, such as a desired $V_H$ segment, a desired D and J or DJ segment and can also include a desired $V_L$ segment. These segments can be taken, for example, from a known antibody that is in need of improvement, such as improved affinity or specificity. The system can be carried out in a model animal, such as a mouse. Moreover, the engineered immune system can be used for optimizing also antigens and, e.g. vaccination methods as well.

The invention is based on, at least in part, on the discovery that the 3'-most $V_H$ segment of the IgH locus is preferentially recombined to form a VDJ segment, but that the native 3'-most $V_H$ segment is selected against. When the native 3'-most $V_H$ segment is replaced with a non-native segment, that non-native segment will be found in a surprisingly large number of the mature antibodies that are produced. Additionally, by rendering the IGCR1 sequence of an IgH locus non-functional, an even larger portion of the antibodies generated from that such an engineered locus will comprise the 3'-most $V_H$ segment. This discovery permits the engineering of antibodies comprising a desired $V_H$ segment while still allowing the antibody to participate in V(D)J recombination, somatic hypermutation, and the germinal center reaction—important processes that contribute to antibody diversity and functionality. The methods and compositions described herein can permit the development of antibodies with improved specificity and/or affinity relative to an antibody generated by existing methods.

In one aspect, described herein is a cell comprising an engineered IgH locus in which the 3'-most $V_H$ segment of the IgH locus is engineered to comprise a cassette targeting sequence. In some embodiments, the cassette targeting sequence permits the replacement of the 3'-most $V_H$ segment. In some embodiments, the cassette targeting sequence is selected from the group consisting of: an I-SceI meganuclease site; a Cas9/CRISPR target sequence; a Talen target sequence or a recombinase-mediated cassette exchange system. In some embodiments, the 3'-most $V_H$ segment of the IgH locus has been engineered to comprise a non-native $V_H$ segment sequence. In one aspect, described herein is a cell comprising an engineered IgH locus, wherein the 3'-most $V_H$ segment has been replaced with a non-native $V_H$ segment.

In some embodiments, the IgH locus is a mouse locus and the 3'-most $V_H$ segment of the IgH locus has been engineered to comprise any $V_H$ segment other than the original mouse 3'-most $V_H$ segment.

In some embodiments, the cell is a mouse embryonic stem cell. In some embodiments, the non-native $V_H$ segment is a human $V_H$ segment. In some embodiments, the non-native $V_H$ segment is a $V_H$ segment from a known antibody in need of improvement of affinity or specificity. In some embodiments, the non-native $V_H$ segment is a human $V_H$ segment from a known antibody in need of improvement of affinity or specificity. In some embodiments, the human $V_H$ segment is IGHV1-2*02, IGV$_H$1-46 or IGHV1-69.

In some embodiments, the cell further comprises a non-functional IGCR1 sequence within the nucleic acid sequence separating the 3' end of the 3'-most $V_H$ segment and the 5' end of a $D_H$ segment. In some embodiments, the non-functional IGCR1 sequence comprises mutated CBE sequences. In some embodiments, the CBE sequences of the IGCR1 sequence have been deleted. In some embodiments, the IGCR1 sequence has been deleted from the IgH locus.

In some embodiments, the cell further comprises a 3' recombinase site being located 3' of the one or more $J_H$ segments; and a passenger cassette being located at the position of a deleted native 3'-most $V_H$ segment, the passenger cassette comprising, from 5' to 3': a 5' recombinase site an inverted passenger VDJ exon and/or a cassette targeting sequence; and a maturation-compatible $V_H$ segment; wherein the recombinase sites are inverted with respect to each other.

In some embodiments, the cell further comprises a 3' recombinase site being located 3' of the one or more $J_H$ segments; and a passenger cassette being located at the position of a deleted native 3'-most $V_H$ segment, the passenger cassette comprising, from 5' to 3': a 5' to 3'-oriented passenger VDJ exon and/or a cassette targeting sequence; a 5' recombinase site; and a maturation-compatible $V_H$ segment; wherein the recombinase sites are in the same orientation.

In some embodiments, the recombinase site is a LoxP site and the cell further comprises a locus encoding cre recombinase. In some embodiments, the locus encoding cre recombinase is under the control of a promoter which is not active in immature B cells and is active in peripheral B cells. In some embodiments, the promoter is the CD21 promoter.

In some embodiments, one or more $D_H$, one or more $J_H$ segments, and/or a $DJ_H$ fusion comprise a cassette targeting sequence. In some embodiments, the IgH locus comprises one or more non-native $D_H$ segments. In some embodiments, the IgH locus comprises one $D_H$ segment. In some embodiments, the IgH locus comprises one or more non-native $J_H$ segments. In some embodiments, the IgH locus comprises one $J_H$ segment. In some embodiments, the IgH locus comprises murine IgH locus sequence. In some embodiments, the IgH locus comprises human IgH locus sequence. In some embodiments, the locus comprises humanized IgH locus sequence. In some embodiments, the $J_H$ locus has been replaced by human D and $J_H$ cassette or a cassette with an assembled human $DJ_H$. In some embodiments, the cell is heterozygous for the engineered IgH locus and the other IgH locus has been engineered to be inactive, wherein the cell will express an IgH chain only from the engineered IgH locus.

In some embodiments, the cell further comprises an IgL locus with human sequence. In some embodiments, the cell further comprises a humanized IgL locus. In some embodiments, the cell further comprises a human IgL locus. In some embodiments, the cell further comprises an IgL locus with one $V_L$ segment. In some embodiments, the cell further comprises an IgL locus with one $J_L$ segment. In some embodiments, the cell further comprises a human rearranged $V_L J_L$ at the IgL kappa or lambda locus. In some embodiments, the cell further comprises a human rearranged $V_L J_L$ at the murine IgL kappa or lambda locus. In some embodiments, the IgL locus encodes IGκV1.

In some embodiments, the cell is a stem cell or an embryonic stem cell. In some embodiments, the cell is a murine cell. In some embodiments, the cell further comprises a mutation capable of activating, inactivating or modifying genes that in a lymphocyte-intrinsic fashion lead to increased GC antibody maturation responses.

In one aspect, described herein is a genetically engineered mouse comprising an engineered cell as described herein. In one aspect, described herein is a chimeric genetically engineered mouse comprising two populations of cells, a first population comprising cells which are V(D)J recombination-defective; and a second population comprising engineered cells as described herein. In some embodiments, the V(D)J recombination-defective cells are RAG2$^{-/-}$ cells. In some embodiments, the mammal is a mouse.

In one aspect, described herein is a method of making an optimized antibody from a known antibody, the method comprising the steps of injecting a mouse blastocyst with an engineered cell as described herein, wherein the cell is a mouse embryonic stem cell, and wherein the $V_H$ segment comprises the $V_H$ segment of the known antibody at the position of the native 3'most $V_H$ segment; implanting the mouse blastocyst into a female mouse under conditions suitable to allow maturation of the blastocyst into a genetically engineered mouse; isolating 1) an optimized antibody comprising the non-native $V_H$ segment; or 2) a cell producing an optimized antibody comprising the non-native $V_H$ segment from the genetically engineered mouse. In some embodiments, the method further comprises a step of immunizing the genetically engineered mouse with a desired target antigen before the isolating step. In some embodiments, the method further comprises a step of producing a monoclonal antibody from at least one cell of the genetically engineered mouse. In some embodiments, the IgH locus of the embryonic stem cell comprises a pre-rearranged $DJ_H$ segment from the known antibody. In some embodiments, the IgL locus of the embryonic stem cell comprises a pre-arranged light chain sequence from the known antibody. In some embodiments, the $V_H$ segment of interest is a germline $V_H$ segment, an affinity maturation intermediate, or a mature $V_H$ segment.

In one aspect, described herein is an optimized antibody produced by any one of the methods described herein.

In one aspect, described herein is a method of producing B lymphocytes comprising $V_H(D)J_H$ rearrangements with a $V_H$ segment from a known monoclonal antibody, the method comprising the steps of: engineering a mouse embryonic stem cell by replacing the most proximal $V_H$ segment of a mouse IgH locus with the $V_H$ segment from a known monoclonal antibody; and injecting the engineered mouse embryonic stem cells into a blastocyst of a mouse which is incapable of forming mature B cells, thereby creating a chimeric mouse that produces B lymphocytes comprising $V_H(D)J_H$ rearrangements comprising the $V_H$ segment from the known monoclonal antibody. In some embodiments, the cells of the blastocyst are V(D)J recombination-defective cells. In some embodiments, the cells of the blastocyst are $RAG2^{-/-}$ cells. In some embodiments, the cells of the blastocyst are not capable of forming mature lymphocytes. In some embodiments, the method further comprises engineering the mouse embryonic stem cell to destroy functionality of the IGCR1 sequence in the nucleic acid sequence separating the 3' end of the most proximal $V_H$ segment. In some embodiments, the engineered cell further comprises IgL sequence from the known monoclonal antibody. In some embodiments, the engineered cell further comprises a $J_H$ locus that has been replaced by a human D and $J_H$ cassette or a cassette with an assembled human $DJ_H$. In some embodiments, the method further comprises a step of breeding the chimeric mouse to produce a mouse that harbors a germline $V_H$ segment from the known antibody. In some embodiments, the ES cell is made homozygous for the human $V_H$ segment. In some embodiments, the human $V_H$ segment consists essentially of a sequence of a $V_H$ segment from a known monoclonal antibody.

In one aspect, described herein is a method of identifying a candidate antigen as an antigen that activates a B cell population comprising a $V_H$ segment of interest, the method comprising: immunizing an engineered mammal as described herein, engineered such that a majority of the mammal's peripheral B cells express the $V_H$ segment of interest, with the antigen; measuring B cell activation in the mammal; and identifying the candidate antigen as an activator of a B cell population comprising the $V_H$ segment of interest if the B cell activation in the mammal is increased relative to a reference level. In some embodiments, an increase in B cell activation is an increase in the somatic hypermutation status of the Ig variable region. In some embodiments, an increase in B cell activation is an increase in the affinity of mature antibodies for the antigen. In some embodiments, an increase in B cell activation is an increase in the specificity of mature antibodies for the antigen. In some embodiments, the $V_H$ segment of interest is a germline $V_H$ segment, an affinity maturation intermediate, or a mature $V_H$ segment.

BRIEF DESCRIPTION OF THE DRAWINGS

FIGS. 1A-1C depict schematics of the constructs described in Example 2 herein.

FIGS. 2A-2D demonstrate the construction and analysis of IGHV1-2*02 constructs.

DETAILED DESCRIPTION OF THE INVENTION

Figure 1A:
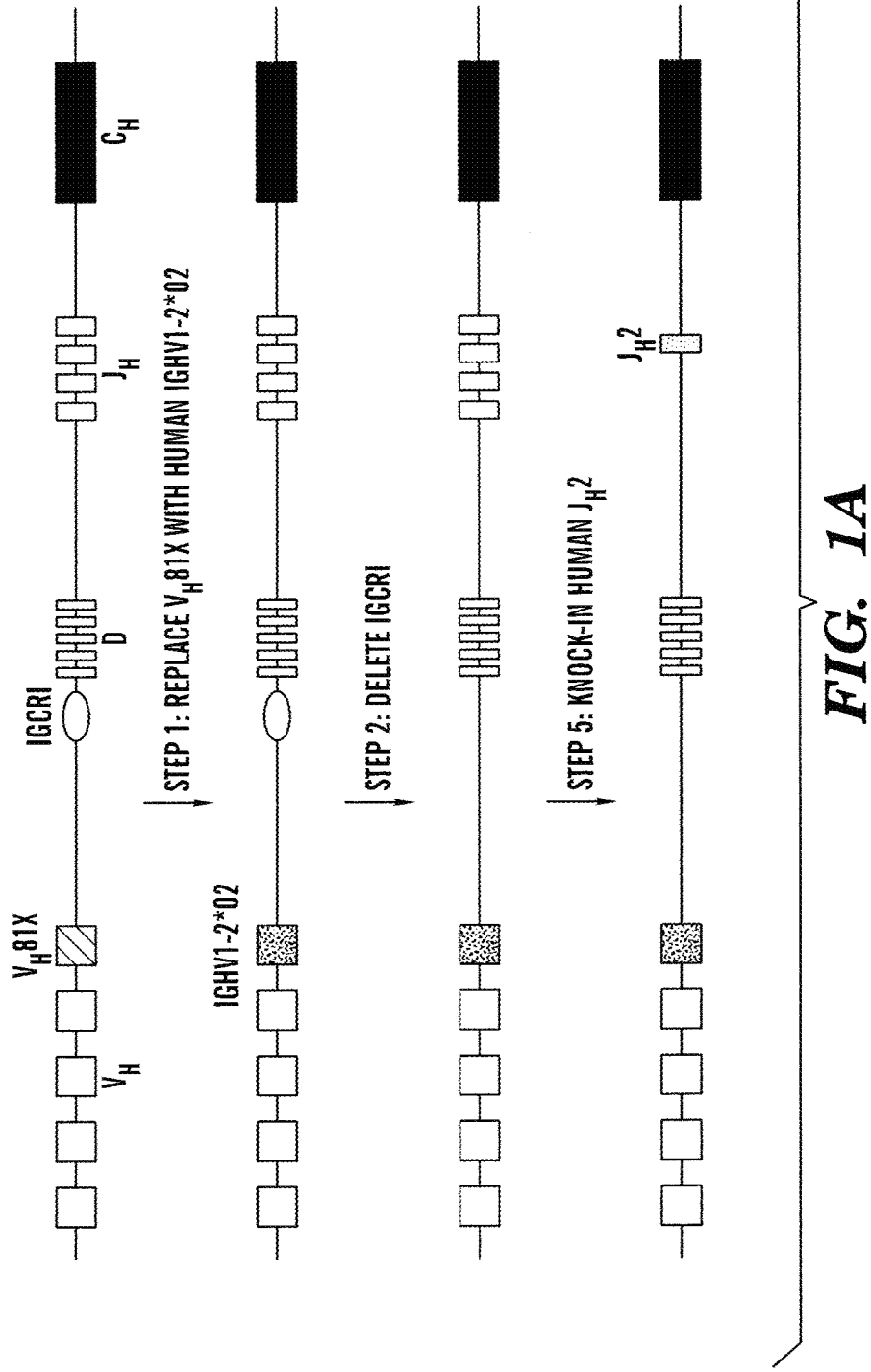

The method and compositions described herein relate to the inventors' discovery that the 3'-most $V_H$ segment of the IgH locus is preferentially recombined with a D segment and $J_H$ segment to form a VDJ segment. However, the inventors have further discovered that antibodies comprising the native murine 3'-most $V_H$ segment ($V_H81X$) are subject to negative selection such that the preferential recombination of $V_H81X$ during V(D)J recombination is not reflected in the makeup of the population of mature antibodies in a wild-type animal. However, when $V_H81X$ is replaced with a non-native $V_H$ segment, that non-native $V_H$ segment is found in a strikingly high number of the mature antibodies which are produced. Accordingly, in one aspect, described herein is a cell comprising an engineered IgH locus, wherein the 3'-most $V_H$ segment has been replaced with a non-native $V_H$ segment. Further provided herein are cells comprising an engineered IgH locus in which the 3'-most $V_H$ segment of the IgH locus is engineered to comprise a cassette targeting sequence, e.g., such that a $V_H$ segment of interest may be readily introduced at the location of the cassette targeting sequence.

As used herein, the term "IgH locus" refers to a locus which either encodes, or can be recombined to encode, the heavy chain polypeptide of an immunoglobin molecule (e.g. a BCR or antibody). Prior to VDJ recombination, an IgH locus comprises, from 5' to 3', one or more $V_H$ segments, one or more $D_H$ segments, and one or more $J_H$ segments and multiple interspersed sequences, e.g. sequences that regulate and/or control the processes of VDJ recombination and expression.

As used herein, the term "$V_H$ segment" refers to the variable segment of an IgH locus. As used herein, the term "$D_H$ segment" or "D segment" refers to a diversity region of an IgH locus. As used herein, the term "$J_H$ segment" refers to a joining region of an IgH locus. One of skill in the art can readily identify such segments within an IgH locus or immunoglobin molecule. By way of non-limiting example, the structure of immunoglobins is discussed in Janeway et al. (eds.)(2001) Immunobiology. Fifth edition, Garland Sciences; Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties During B cell development, an IgH $D_H$ segment is recombined with a $J_H$ segment, physically joining them together to form a "$DJ_H$ rearrangement". A next step in B cell development recombines a $V_H$ segment with the $DJ_H$ rearrangement to form a "$V_H DJ_H$ rearrangement." That is, a "$V_H DJ_H$ rearrangement" or "$DJ_H$ rearrangement" is a polynucleotide in which the named segments are recombined and intervening sequences found in the germline have been removed. Such rearrangements can be native constructs found in B cells or constructs created in vitro and optionally introduced into a cell.

A segment of an Ig gene, e.g., a $V_H$ segment can be, e.g. a germline $V_H$ segment, an affinity maturation intermediate, or a mature $V_H$ segment. In some embodiments, a germline $V_H$ segment can be a $V_H$ segment as found in the genome of a germline cell, e.g. prior to any V(D)J recombination event. In some embodiments, a maturation intermediate can be a $V_H$ segment after at least one V(D)J recombination event but prior to the completion of the GC reaction and/or SHM. In some embodiments, a mature $V_H$ segment can be a $V_H$ segment as found in a mature B-cell. A $V_H$ segment, as comprised by a maturation intermediate or a mature $V_H$ segment, is present in the cell as a VDJ rearrangement, having been recombined with a $DJ_H$ rearrangement.

As used herein, the term "native" refers to the sequence found in a particular location in the genome of a non-engineered cell and/or animal. As used herein, the term "non-native" refers to a sequence which varies from the sequence found in a particular location in the genome of a non-engineered cell and/or animal. A non-native sequence can be, e.g. a sequence from a different species or a sequence from the same species which has been moved to a non-native position in the genome. Thus, while a sequence may be "native" to a particular gene in the genome of an un-engineered cell, if it has been moved within the gene in an engineered cell, it is no longer considered native. In some embodiments, a non-native sequence differs from the native sequence by, at least 5%, e.g. at least 5%, at least 10%, at least 20%, at least 30%, at least 40%, at least 50% or more. In some embodiments, the IgH locus is a mouse locus and the 3'-most $V_H$ segment of the IgH locus has been engineered to comprise any $V_H$ segment other than the original mouse 3'-most (i.e. most 3' proximal or closest to the 3' end) $V_H$ segment. In some embodiments, the non-native $V_H$ segment is a human $V_H$ segment. In some embodiments, the non-native $V_H$ segment is a $V_H$ segment from a known antibody in need of improvement of affinity or specificity. In some embodiments, the non-native $V_H$ segment is a human $V_H$ segment from a known antibody in need of improvement of affinity or specificity.

While the methods and compositions described herein are suitable for use with any $V_H$ segment, certain $V_H$ segments are particularly contemplated for use in the compositions and methods described herein due to their known antigen specificities. In some embodiments of any of the aspects described herein, the $V_H$ segment can be selected from the group consisting of: IGHV1-2*02, IGV$_H$1-46 or IGHV1-69. The sequences of these $V_H$ segments are known in the art, for example, IGHV1-2*02 is described by Genbank Accession No: FN550184.1 (SEQ ID NO: 1) and SEQ ID NO: 13 of International Patent Publication WO 2010/054007; and IGV$_H$1-46 is described by Genbank Accession No: AJ347091.1 (SEQ ID NO: 2).

As used herein, the term "cassette targeting sequence" refers to a sequence that permits a sequence of interest (e.g. a sequence comprising a $V_H$ segment of interest), to be inserted into the genome at the location of the cassette targeting sequence via the action of at least one enzyme that targets the cassette targeting sequence. Non-limiting examples of cassette targeting sequences are an I-SceI meganuclease site; a Cas9/CRISPR target sequence; a Talen target sequence; a zinc finger nuclease (ZFN) and a recombinase-mediated cassette exchange system. Such cassette targeting systems are known in the art, see, e.g. Clark and Whitelaw Nature Reviews Genetics 2003 4:825-833; which is incorporated by reference herein in its entirety. In some embodiments, the cassette targeting sequence permits the replacement of the 3'-most $V_H$ segment.

I-SceI, Zinc finger nucleases (ZFNs), the Cas9/CRISPR system, and transcription-activator like effector nucleases (TALENs) are nucleases. Nucleases are found commonly in microbial species and have the unique property of having very long recognition sequences (>14 bp) thus making them naturally very specific for cutting at a desired location. This can be exploited to make site-specific double-stranded breaks in, e.g. a genome. These nucleases can cut and create specific double-stranded breaks at a desired location(s) in the genome, which are then repaired by cellular endogenous processes such as, homologous recombination (HR), homology directed repair (HDR) and non-homologous end-joining (NHEJ). NHEJ directly joins the DNA ends in a double-stranded break, while HDR utilizes a homologous sequence as a template for regenerating the missing DNA sequence at the break point. Thus, by introducing, e.g., a ZFN, CRISPR, and/or TALENs specific for the cassette targeting sequence into a cell, at least one double strand-break can be generated in the genome, resulting in a template sequence, e.g. a sequence comprising a $V_H$ segment of interest, being used to repair the break, thereby introducing the template sequence into the genome and the desired location (see, e.g. Gaj et al. Trends in Biotechnology 2013 31:397-405; Carlson et al. PNAS 2012 109:17382-7; and Wang et al. Cell 2013 153: 910-8; each of which is incorporated by reference herein in its entirety).

Mutagenesis and high throughput screening methods have been used to create nuclease and/or meganuclease variants that recognize unique sequences. For example, various nucleases have been fused to create hybrid enzymes that recognize a new sequence. Alternatively, DNA interacting amino acids of the nuclease can be altered to design sequence specific nucleases (see e.g., U.S. Pat. No. 8,021, 867). Nucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, nucleases with site specific cutting characteristics can be obtained using commercially available technologies e.g., Precision BioSciences' Directed Nuclease Editor™ genome editing technology.

ZFNs and TALENs restriction endonuclease technology utilizes a non-specific DNA cutting enzyme which is linked to a specific DNA sequence recognizing peptide(s) such as zinc fingers and transcription activator-like effectors (TALEs). Typically an endonuclease whose DNA recognition site and cleaving site are separate from each other is selected and its cleaving portion is separated and then linked to a sequence recognizing peptide, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

In some embodiments, the Cas9/CRISPR system can be used to introduce sequences at a cassette targeting sequence as described herein. Clustered regularly interspaced short palindromic repeats (CRISPR)/CRISPR-associated (Cas) systems are useful for, e.g. RNA-programmable genome editing (see e.g., Marraffini and Sontheimer. Nature Reviews Genetics 2010 11:181-190; Sorek et al. Nature Reviews Microbiology 2008 6:181-6; Karginov and Hannon Mol Cell 2010 1:7-19; Hale et al. Mol Cell 2010:45:292-302; Jinek et al. Science 2012 337:815-820; Bikard and Marraffini Curr Opin Immunol 2012 24:15-20; Bikard et al. Cell Host & Microbe 2012 12:177-186; all of which are incorporated by reference herein in their entireties). A CRISPR guide RNA is used that can target a Cas enzyme to the desired location in the genome, where it generates a double strand break. This technique is known in the art and described, e.g. at Mali et al. Science 2013 339:823-6; which is incorporated by reference herein in its entirety and kits for the design and use of CRISPR-mediated genome editing are commercially available, e.g. the PRECISION X CAS9 SMART NUCLEASE™ System (Cat No. CAS900A-1) from System Biosciences, Mountain View, CA.

In some embodiments, a CRISPR, TALENs, or ZFN molecule (e.g. a peptide and/or peptide/nucleic acid complex) can be introduced into a cell, e.g. a cultured ES cell, such that the presence of the CRISPR, TALENs, or ZFN molecule is transient and will not be detectable in the progeny of, or an animal derived from, that cell. In some embodiments, a nucleic acid encoding a CRISPR, TALENs, or ZFN molecule (e.g. a peptide and/or multiple nucleic acids encoding the parts of a peptide/nucleic acid complex) can be introduced into a cell, e.g. a cultured ES cell, such that the nucleic acid is present in the cell transiently and the nucleic acid encoding the CRISPR, TALENs, or ZFN molecule as well as the CRISPR, TALENs, or ZFN molecule itself will not be detectable in the progeny of, or an animal derived from, that cell. In some embodiments, a nucleic acid encoding a CRISPR, TALENs, or ZFN molecule (e.g. a peptide and/or multiple nucleic acids encoding the parts of a peptide/nucleic acid complex) can be introduced into a cell, e.g. a cultured ES cell, such that the nucleic acid is maintained in the cell (e.g. incorporated into the genome) and the nucleic acid encoding the CRISPR, TALENs, or ZFN molecule and/or the CRISPR, TALENs, or ZFN molecule will be detectable in the progeny of, or an animal derived from, that cell.

Recombinase-mediated cassette exchange systems (RMCEs) utilize recombinases (e.g. Flp) and the sequences recognized by the recombinases (e.g., FRT target sites) to swap sequences from the genome, flagged by the FRT target sites with sequences in a cassette that are likewise flanked by the FRT target sites. RMCEs are known in the art, e.g., Cesari et al. Genesis 2004 38:87-92 and Roebroek et al. Mol Cell Biol 2006 26:605-616; each of which is incorporated by reference herein in its entirety.

The inventors have further discovered that rendering the IGCR1 sequence of an IgH locus non-functional causes the 3'-most $V_H$ segment to be recombined into a VDJ segment at an even higher rate. In some embodiments, the engineered IgH gene comprises a non-functional IGCR1 sequence. As used herein, "intergenic control region 1" or "IGCR1" refers to a region located in the IgH locus the 3' end of the 3'-most native $V_H$ segment and the 5' end of the 5'-most native DH segment and controls VDJ recombination. The IGCR1 is approximately 4.1 kb in length The IGCR1 comprises two CTCF-binding elements (CBEs) that are required for IGCR1 function. The structure of IGCR1 and the CBEs is explained in more detail, e.g., in Guo et al. Nature 2011 477-424-431; which is incorporated by reference herein in its entirety. A non-functional IGCR1 sequence can be an IGCR1 sequence which has 50% or less of the wild-type activity, e.g., 50% or less ability to form VDJ rearrangements with $V_H$ segments other than the 3'-most $V_H$ segment. Methods of measuring the rate of VDJ rearrangements comprising any given segment are known in the art, e.g., by PCR using probes specific for a particular segment (see, e.g., Guo et al. Nature 2011 477-424-431).

In some embodiments, a non-functional IGCR1 sequence is one in which at least one CBE sequence has been deleted. In some embodiments, a non-functional IGCR1 sequence is one in which both CBE sequences have been deleted. In some embodiments, a non-functional IGCR1 sequence is one in which the IGCR1 sequence has been deleted, e.g. the 4.1 kb comprising IGCR1 has been deleted. In some embodiments, a non-functional IGCR1 sequence is one in which one or more CBE sequences have been deleted, e.g., the 2.6 kb sequence comprising both CBE sequences has been deleted, or any portion of that 2.6 kb sequence comprising at least one CBE sequence has been deleted.

In some embodiments, a non-functional IGCR1 sequence is one in which one or more CBE sequences have been mutated. Mutating the sequence of a CBE sequence, such that CTCF binding is reduced by at least 25% (e.g. reduced by 25% or more, 50% or more, or 75% or more) can render the IGCR1 non-functional. Binding of CTCF to a given mutated CBE can be readily measured, e.g., by southern blotting. Non-limiting examples of such mutations are described, e.g., in Guo et al. Nature 2011 477-424-431; which is incorporated by reference herein in its entirety.

It can be difficult to isolate and/or produce antibodies comprising a particular $V_H$ segment because that $V_H$ segment is selected against, e.g. if that $V_H$ segment is particularly likely to recognize a self-antigen, B-cells with the $V_H$ segment are more likely to be selected against. Such $V_H$ segments are termed "maturation-incompatible" herein. This term does not imply that B-cells expressing a BCR and/or antibody comprising such a $V_H$ segment are invariably subject to clonal deletion and/or anergy. Provided herein are methods and compositions for avoiding clonal deletion and/or anergy during B-cell development and causing B-cells to express a maturation-incompatible $V_H$ segment at a desired timepoint in development, e.g. after clonal deletion and/or anergy is likely to occur. These methods and compositions involve inserting a passenger VDJ exon into a IgH locus in such a manner that while present in the locus, it will be neither expressed nor removed by normal IgH V(D)J recombination. A B cell comprising the passenger VDJ exon will express a second, maturation-compatible, VDJ exon (e.g. one generated by IgH V(D)J recombination) and at a desired time, the sequence of the locus can be manipulated to cause the passenger VDJ exon to be expressed instead of the maturation-compatible exon. As used herein, a "passenger" exon is an exon that is present in the germline and mature B-cell genome but is not expressed until the genome is subjected to an induced recombination event, e.g. an Cre-mediated recombination event.

In a first approach, the maturation-incompatible $V_H$ segment (e.g. as part of a passenger VDJ exon) is inserted into the IgH locus in a 3' to 5' conformation relative to the IgH locus and is located 5' of the maturation-compatible VDJ exon (or the sequences that will be recombined to make the maturation-compatible VDJ exon). Expression of the passenger VDJ exon is induced by the use of a pair of inverted recombinase sites, which cause the passenger VDJ exon to be "flipped" so that it is in the 5' to 3' orientation with respect to the rest of the IgH locus. In some embodiments, described herein is a cell comprising a 3' recombinase site being located 3' of the one or more $J_H$ segments; and a passenger cassette being located at the position of a deleted native 3'-most $V_H$ segment, the passenger cassette comprising, from 5' to 3' 1) a 5' recombinase site 2) an inverted passenger VDJ exon or a cassette targeting sequence; and 3) a maturation-compatible $V_H$ segment; wherein the recombinase sites are inverted with respect to each other.

In a second approach, the maturation-incompatible $V_H$ segment, (e.g. as part of a passenger VDJ exon) is inserted 5' to 3' with respect to the IgH locus and V(D)J recombination occurs downstream of the passenger exon to generate a maturation-compatible VDJ exon. The maturation-compatible VDJ exon can then be excised by inducing recombination (e.g., Cre-mediated recombination) at a pair of recombinase sites when desired, causing the cell to express the passenger exon. In some embodiments, described herein is a cell comprising a 3' recombinase site being located 3' of the one or more $J_H$ segments; and a passenger cassette being located at the position of a deleted native 3'-most $V_H$ segment, the passenger cassette comprising, from 5' to 3': 1)

a passenger VDJ exon or a cassette targeting sequence; 2) a 5' recombinase site; and 3) a maturation-compatible $V_H$ segment.

Recombination sites and systems for inducing recombination at these sites are known in the art, e.g. the cre-Lox system or the Flp recombinase. The loxP-Cre system utilizes the expression of the PI phage Cre recombinase to catalyze the excision or inversion of DNA located between flanking lox sites. By using gene-targeting techniques to produce binary transgene animals with modified endogenous genes that can be acted on by Cre or Flp recombinases expressed under the control of tissue-specific promoters, site-specific recombination may be employed to excise or invert sequences in a spatially or time controlled manner. See, e.g., U.S. Pat. Nos. 6,080,576, 5,434,066, and 4,959,317; and Joyner, A. L., et al. Laboratory Protocols for Conditional Gene Targeting, Oxford University Press, New York (1997); Orban et al. (1992) PNAS 89:6861-6865; Aguzzi A, Brandner S, Isenmann S, Steinbach J P, Sure U. Glia. 1995 November; 15(3):348-64. Review; each of which is incorporated by reference herein in its entirety.

In some embodiments, the cell further comprises a gene encoding a recombinase that will induce recombination at the recombinase site. In some embodiments, the recombinase site is a LoxP site. In some embodiments, the cell further comprises a gene encoding cre recombinase. A gene encoding a recombinase can be under the control of, e.g. an inducible promoter or a cell-specific promoter. Inducible promoters, temporally-specific, and tissue-specific promoters for the control of a recombinase are known in the art. In some embodiments, the gene encoding a recombinase is under the control of a promoter which is not active in immature B cells and is active in peripheral B cells, e.g. the CD21 promoter, CD19 promoter, CD84 promoter, CD24 promoter, CD45R promoter.

If a particular $J_H$ segment, D segment, assembled $DJ_H$ segment, $V_L$ segment, $J_L$ segment, assembled $V_LJ_L$ segment, and/or light chain sequence is desired to be present in the mature antibody or antibodies produced by a cell and/or animal described herein, the IgH and/or IgL locus can be further engineered to comprise such a sequence of interest. In some embodiments, the locus can be engineered to comprise the sequence of interest such that it is one possible segment of its type that can be recombined to form a mature antibody sequence (e.g. a human $J_H$ segment can be introduced into a murine IgH locus while retaining at least one native mouse $J_H$ segment). In some embodiments, the locus can be engineered to comprise the sequence of interest such that it will be the segment of its type that will be present in all mature antibody sequences (e.g., a human $J_H$ segment can be introduced into a murine IgH locus such that all native murine $J_H$ segments are deleted or disabled).

In some embodiments, the $J_H$ locus can be replaced by a human D and $J_H$ cassette or a cassette with an assembled human $DJ_H$. In some embodiments, one or more $D_H$, one or more $J_H$ segments, and/or a $DJ_H$ fusion comprise a cassette targeting sequence. In some embodiments, the IgH locus comprises one or more non-native $D_H$ segments. In some embodiments, the IgH locus comprises one $D_H$ segment. In some embodiments, the IgH locus comprises one or more non-native $J_H$ segments. In some embodiments, the IgH locus comprises one $J_H$ segment. In some embodiments, the IgH locus comprises murine IgH locus sequence. In some embodiments, the IgH locus comprises human IgH locus sequence. In some embodiments, the locus comprises humanized IgH locus sequence.

In some embodiments, the cell is heterozygous for the engineered IgH locus as described herein and the other IgH locus has been engineered to be inactive, wherein the cell will express an IgH chain only from the engineered IgH locus as described herein. The inactive IgH locus can be, by way of non-limiting example, deleted, partially deleted, and/or mutated (e.g. the IGCR1 sequence can be mutated and/or deleted or sequences necessary for V(D)J recombination can be mutated and/or deleted (e.g. deleting the $J_H$ portion of the locus)).

In some embodiments, a cell described herein can comprise an IgL locus with human sequence. In some embodiments, a cell described herein can comprise a humanized IgL locus. In some embodiments, a cell described herein can comprise a human IgL locus. In some embodiments, a cell described herein can comprise an IgL locus with one $V_L$ segment. In some embodiments, a cell described herein can comprise an IgL locus with one $J_L$ segment. In some embodiments, a cell described herein can comprise a human rearranged $V_LJ_L$ at the IgL locus. In some embodiments, the IgL gene encodes IGκV1.

The methods and compositions described herein can relate to the production of antibodies in a manner that capitalizes on the variation produced by, e.g., the GC response and SHM. In some embodiments, a cell described herein can further comprise a mutation capable of activating, inactivating or modifying genes that in a lymphocyte-intrinsic fashion lead to increased GC antibody maturation responses. Such mutations are known in the art and can include, by way of non-limiting example $PTEN^{-/-}$ (see, e.g., Rolf et al. Journal of Immunology 2010 185:4042-4052; which is incorporated by reference herein in its entirety) and mutations or modifications of QA-1 (see, e.g. L. Lu et al., Proc. Natl. Acad. Sci. USA. 105, 19420 (2008) and H. J. Kim et al., Nature 467, 328 (2010); each of which is incorporated by reference herein in its entirety).

A cell as described herein can be, by way of non-limiting example, a stem cell, an embryonic stem cell, a B cell, a mature B cell, an immature B cell, and/or a hybridoma cell. A cell as described herein can be, by way of non-limiting example, a mammalian cell, a human cell, and/or a mouse cell. In some embodiments, a cell as described herein can be a mouse embryonic stem cell.

In one aspect, described herein is genetically engineered mammal comprising an engineered cell as described herein. In some embodiments, the mammal can be a mouse. In some embodiments, the methods described herein, e.g. methods of producing antibodies and/or testing antigens require only that the B-cells of the genetically engineered mammal are engineered as described herein. Accordingly, in some embodiments, the genetically engineered mammal can be a chimera, e.g. it can comprise two genetically distinct populations of cells. The use of chimeras can expedite the process of obtaining a genetically engineered mammal to be used in the methods described herein. In one aspect, described herein is a chimeric genetically engineered mammal, e.g. a mouse, comprising two populations of cells, a first population comprising cells which are V(D)J recombination-defective; and a second population comprising engineered cells as described herein. V(D)J recombination-defective cells are known in the art, e.g. $RAG2^{-/-}$ cells.

The cells and mammals described herein permit the optimization of known antibodies. By engineering the cell and/or mammal to express antibodies (which are subject to V(D)J recombination, the GC reaction, and/or SHM), comprising segment(s) known to recognize a particular antigen (e.g. segment(s) from a known antibody that recognizes the particular antigen), a large number of antibodies can be generated which are related to the known antibody. These antibodies can be screened and/or selected, in vitro and/or in vivo for optimized characteristics relative to the known antibody. Optimization can be an increase in, e.g. affinity, and/or specificity.

In one aspect, described herein is method of making an optimized antibody from a known antibody, the method comprising the steps of: injecting a mouse blastocyst with a cell as described herein, wherein the cell is a mouse embryonic stem cell, and wherein the $V_H$ segment comprises the $V_H$ segment of a known antibody at the position of the native 3'most $V_H$ segment; implanting the mouse blastocyst into a female mouse under conditions suitable to allow maturation of the blastocyst into a genetically engineered mouse; and isolating 1) an optimized antibody comprising the non-native $V_H$ segment; or 2) a cell producing an optimized antibody comprising the non-native $V_H$ segment from the genetically engineered mouse. In some embodiments, the blastocyst cells are V(D)J recombination-defective cells, e.g. RAG2$^{-/-}$ cells. In some embodiments, the IgH loci of the blastocyst cells have been rendered non-functional, as described elsewhere herein (e.g. the $J_H$ sequences of the IgH loci of the blastocyst cells have been deleted). In some embodiments, the blastocyst cells are not capable of forming mature B cells, and optionally are not capable of forming mature T-cells. In some embodiments, the blastocyst cells are not capable of forming mature lymphocytes.

In some embodiments, the method can further comprise a step of immunizing the genetically engineered mouse with a desired target antigen before the isolating step. In some embodiments, the method can further comprise a step of producing a monoclonal antibody from at least one cell of the genetically engineered mouse.

In some embodiments, the IgH locus of the embryonic stem cell comprises a pre-rearranged $DJ_H$ segment from the known antibody. In some embodiments, the IgL locus of the embryonic stem cell comprises a pre-arranged light chain sequence from the known antibody. In some embodiments, the $V_H$ segment of interest is a germline $V_H$ segment, an affinity maturation intermediate, or a mature $V_H$ segment.

Once the cell as described herein is produced through the methods described herein, an animal can be produced from this cell through either stem cell technology or cloning technology. For example, if the cell into which the nucleic acid was transfected was a stem cell for the organism (e.g. an embryonic stem cell), then this cell, after transfection and culturing, can be used to produce an organism which will contain the engineered aspects in germline cells, which can then in turn be used to produce another animal that possesses the engineered aspects in all of its cells. In other methods for production of an animal containing the engineered aspects, cloning technologies can be used. These technologies generally take the nucleus of the engineered cell and either through fusion or replacement fuse the engineered nucleus with an oocyte which can then be manipulated to produce an animal. The advantage of procedures that use cloning instead of ES technology is that cells other than ES cells can be transfected. For example, a fibroblast cell, which is very easy to culture can be used as the cell which is engineered, and then cells derived from this cell can be used to clone a whole animal.

Generally, cells (e.g. ES cells) used to produce the engineered animals will be of the same species as the animal to be generated. Thus for example, mouse embryonic stem cells will usually be used for generation of engineered mice. Methods of isolating, culturing, and manipulating various cells types are known in the art. By way of non-limiting example, embryonic stein cells are generated and maintained using methods well known to the skilled artisan such as those described by Doetschman et al. (1985) J. Embryol. Exp. Mol. Biol. 87:27-45). The cells are cultured and prepared for genetic engineering using methods well known to the skilled artisan, such as those set forth by Robertson in: Teratocarcinomas and Embryonic Stem Cells: A Practical Approach, E. J. Robertson, ed. IRl. Press, Washington, D.C., [1987]); by Bradley et al. (1986) Current Topics in Devel. Biol. 20:357-371); and by Hogan et al. (Manipulating the Mouse Embryo: A Laboratory Manual, Cold Spring Harbor Laboratory Press, Cold Spring Harbor. N.Y. (1986)).

In some embodiments, after cells comprising the engineered aspects have been generated, and optionally, selected, the cells can be inserted into an embryo or blastocyst, e.g. to generate a chimera. Insertion may be accomplished in a variety of ways known to the skilled artisan, however the typical method is by microinjection. For microinjection, about 10-30 cells are collected into a micropipet and injected into embryos that are at the proper stage of development to permit integration of the engineered ES cell into the developing embryo or blastocyst. For instance, the ES cells can be microinjected into blastocysts. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

Methods of isolating antibodies and/or antibody-producing cells are known in the art, and can include, by way of non-limiting example, producing a monoclonal antibody via, e.g., the production of hybridomas or phage display. See, e.g., Little et al. Immunology Today 2000 21:364-370; Pasqualini et al. PNAS 2004 101:257-259; Reichert et al. Nature Reviews Drug Discovery 2007 6:349-356; and Wang et al. Antibody Technology Journal 2011 1:1-4; each of which is incorporated by reference herein in its entirety.

In one aspect, described herein is an optimized antibody produced by the method described above herein.

In one aspect, described herein is a method of producing B lymphocytes comprising $V_H(D)J_H$ rearrangements with a $V_H$ segment from a known monoclonal antibody, the method comprising the steps of: engineering a mouse embryonic stem cell by replacing the most proximal $V_H$ segment of a mouse IgH locus with the $V_H$ segment from a known monoclonal antibody; and injecting the engineered mouse embryonic stem cells into a blastocyst of a mouse thereby creating a chimeric mouse that produces B lymphocytes comprising $V_H(D)J_H$ rearrangements comprising the $V_H$ segment from the known monoclonal antibody. In some embodiments, the method can further comprise engineering the mouse embryonic stem cell to destroy functionality of the IGCR1 sequence in the nucleic acid sequence separating the 3' end of the most proximal $V_H$ segment. Mutations and/or alterations that render the IGCR1 sequence non-functional are described elsewhere herein. In some embodiments, the blastocyst cells are V(D)J recombination-defective cells, e.g. RAG2$^{-/-}$ cells. In some embodiments, the IgH loci of the blastocyst cells have been rendered non-functional, as described elsewhere herein (e.g. the $J_H$ sequences of the IgH loci of the blastocyst cells have been deleted). In some embodiments, the blastocyst cells are not capable of forming mature B cells, and optionally are not capable of forming mature T-cells. In some embodiments, the blastocyst cells are not capable of forming mature lymphocytes.

In some embodiments, the mouse embryonic stem cell is further engineered to comprise IgL sequence from the known monoclonal antibody. In some embodiments, the mouse embryonic stem cell is further engineered to comprise a $J_H$ locus that has been replaced by a human D and $J_H$ cassette or a cassette with an assembled human $DJ_H$.

In some embodiments, the method further comprises a step of breeding the chimeric mouse to produce a mouse that harbors a germline $V_H$ segment from the known antibody. In some embodiments, the ES cell is made homozygous for the human $V_H$ segment. In some embodiments, the human $V_H$ segment consists essentially of a sequence of a $V_H$ segment from a known monoclonal antibody.

As described elsewhere herein, certain vaccine development strategies rely upon identifying one or more intermediate antigens, such that immunization with the one or more intermediate antigens will trigger B cell activation and diversification of antibodies, resulting in the production of an antibody that will recognize the final target antigen (e.g. an HIV antigen). Accordingly, described herein are methods and compositions that permit the in vivo evaluation of such intermediate antigens. In some embodiments, structural information about antibodies that will recognize the final target antigen is known, e.g. what $V_H$ segment is comprised by antibodies to HIV antigens in those rare subjects with a natural antibody defense against HIV. Using the methods and compositions described herein, the ability of an intermediate antigen to activate B cells comprising antibodies with such a $V_H$ segment can be assessed, permitting the development of multiple antigen immunization therapies.

In one aspect, described herein is a method of identifying a candidate antigen as an antigen that activates a B cell population comprising a $V_H$ segment of interest, the method comprising: immunizing an engineered mammal as described herein, engineered such that a majority of the mammal's peripheral B cells express the $V_H$ segment of interest, with the antigen; measuring B cell activation in the mammal; and identifying the candidate antigen as an activator of a B cell population comprising the $V_H$ segment of interest if the B cell activation in the mammal is increased relative to a reference level. B cell activation can be, e.g. an increase in the somatic hypermutation status of the Ig variable region, an increase in the affinity of mature antibodies for the antigen, and/or an increase in the specificity of mature antibodies for the antigen.

For example, the methods as described, can be used to make and test better vaccines, such as HIV or influenza vaccines.

For example, an HIV vaccine field would benefit from better mouse models to test in vivo immunization strategies to elicit therapeutically effective anti-HIV broadly neutralizing antibodies (bNABs) (1). Our novel and rapid approach, based on RAG-2 deficient blastocyst complementation (RDBC) method, can be used to generate chimeric mice expressing in their B cells specific human antibodies of interest to the HIV vaccine field for use in vaccination studies. This mouse model can facilitate studies of the efficacy of immunogens to stimulate affinity maturation of precursor antibodies into BnAbs.

Figure 2A:
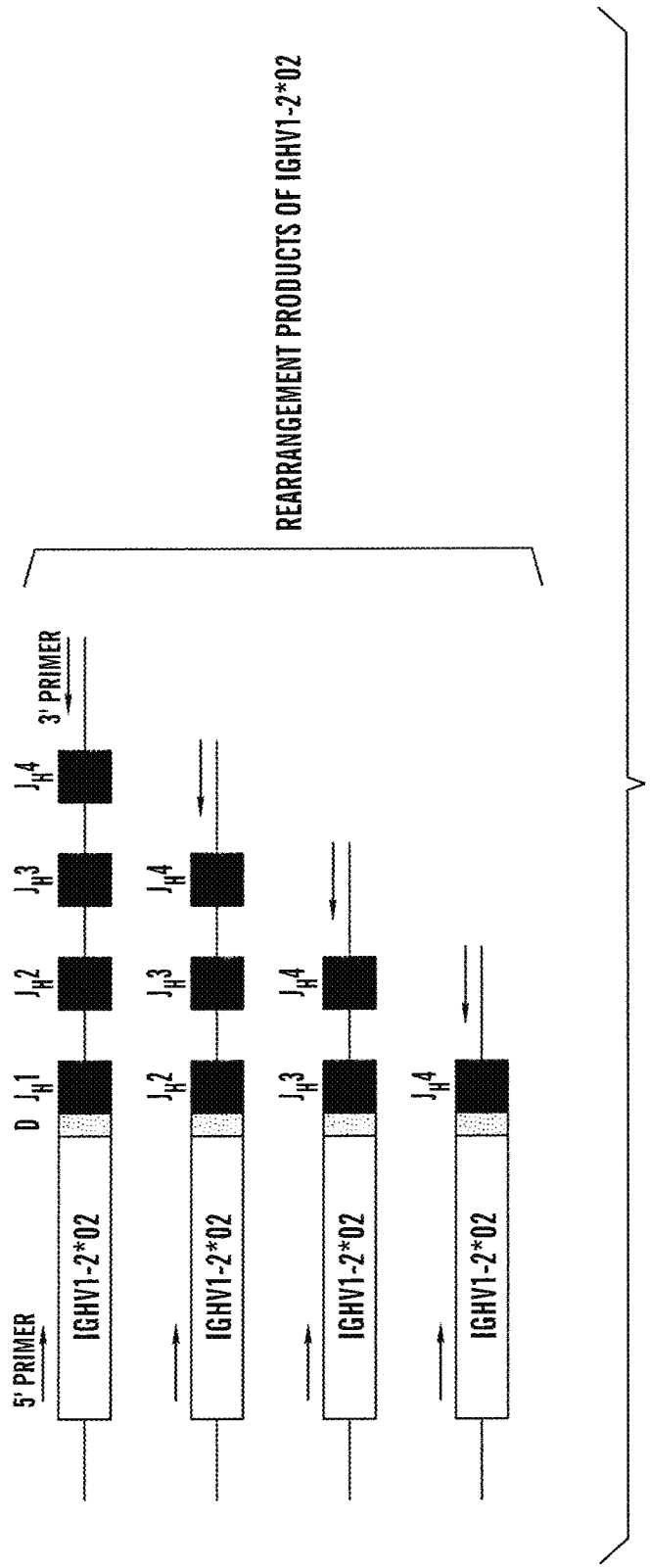

For example, we have created a mouse model that expresses the unmutated precursor of VRC01. The germline $V_H$ segment of VRC01 is IGHV1-2*02 (2). To express IGHV1-2*02 in mice, homology-mediated gene-targeting was used to substitute IGHV1-2*02 for mouse $V_H 81X$ in mouse embryonic stem (ES) cells (FIG. 1A, step 1). Since $V_H 81X$ is the most frequently utilized mouse $V_H$ segment for V(D)J recombination (3), it was postulated that IGHV1-2*02 would experience the same rearrangement preference when inserted in place of $V_H 81X$. Mice that contain the IGHV1-2*02 replacement were generated. In these mice, approximately 4% of B cells harbored rearranged IGHV1-2*02 (FIGS. 2A and 2B). Given that the mouse IgH locus contains more than 100 $V_H$ segments, this result indicates that IGHV1-2*02 is preferentially utilized for V(D)J recombination in this mouse model.

One can also modify the $V_H 81X$ locus so that any human $V_H$ segment introduced into this locus will undergo efficient rearrangement and dominate the repertoire of mature B cells in peripheral lymphoid tissues.

One can further integrate human $DJ_H$ or $J_H$ segments of BnAbs into the mouse $J_H$ locus so that they can be joined to the human $V_H$ segments at $V_H 81X$ locus. In addition, one can modify the mouse $J_H$ locus to facilitate the introduction of other human $J_H$ segments into the locus in the future to express the human Ig light chain (IgL) of BnAbs by integrating a pre-rearranged version of the IgL variable region into the mouse Igk locus.

One can use the system described herein to express affinity maturation intermediates of VRC01. These mice allow sequential immunization of an unmutated ancestor or mutation intermediates that guide affinity maturation toward fully mature BnAbs.

In some aspects, one can delete the IGCRI element. IGCRI is a regulatory element in the intervening region between $V_H$ and Ds (5). Deletion of IGCRI accentuates the biased utilization of $V_H 81X$ for V(D)J recombination (5). IGCRI was deleted from the IgH allele into which IGHV1-2*02 was incorporated (FIG. 1A step 2). The IGHV1-2*02/IGCRID ES cells were injected into Rag2 deficient blastocysts to generate chimeric mice. Since Rag2 is essential for V(D)J recombination, B and T cells can only derive from the Rag2 sufficient ES clones, but not from the Rag2 deficient blastocysts (4). This RDBC method permits the evaluation of the impact of any genetic manipulation of ES cells on B and T cells in chimeric mice. The frequency of IGHV1-2*02 usage in mature B cells in the IGHV1-2*02/IGCRID chimeric mice was determined (FIGS. 2A and 2B). Based on hybridoma analysis, 59% of splenic B cells contained rearranged IGHV1-2*02. Thus, deletion of IGCRI increased usage of IGHV1-2*02 by 15-fold. Recombination joints involving IGHV1-2*02 were sequenced and it was found that 20% were productive (FIG. 2C). Without wishing to be bound by theory, non-productive IGHV1-2*02 rearrangements were carried through B cell development by productive rearrangements of the other IgH allele.

In some aspects, one can delete the $J_H$ region of the $IgH^b$ allele. To limit V(D)J recombination to the IgH allele containing IGHV1-2*02, we deleted the $J_H$ region of the other IgH allele. The ES cell used herein derives from an F1 hybrid between 129 and C57BL/6 mice. The IgH alleles of 129 and C57BL/6 mice belong to the $IgH^a$ and $IgH^b$ allotypes respectively; IGHV1-2*02 replacement and IGCRI deletion occurred on the $IgH^a$ allele. To inactivate the $IgH^b$ allele, the $J_H^b$ region was deleted (FIG. 1B, step 3) and the manipulated ES cells were used for RDBC. The frequency of IGHV1-2*02 usage among splenic B cells in IGHV1-2*02/IGCRID/$J_H^b$ RDBC mice was determined and it was found that 34% of the B cells contained IGHV1-2*02 rearrangements, all of which were productive (FIGS. 2A-2D). Thus, the IGHV1-2*02/IGCRID/$J_H^b$ ES clone can serve as an efficient platform to express any human $V_H$ segment in mouse models.

In some aspects, one incorporates the Ig light chain (IgL) for the unmutated precursor of VRC01 into mouse Jk locus.

The signature of the IgL chain for the VRC01 family of BnAbs is a short 5-amino acid CDR L3 (6). As the chance of obtaining such short CDR L3 through de novo rearrangement is low, a pre-rearranged version of unmutated VRC01 IgL was integrated into the mouse $Jk^a$ locus (FIG. 1C, step 4). The ES clone (IGHV1-2*02/IGCRID/$J_H^b$DNRC01LC) was injected into Rag2 deficient blastocysts to generate chimeric mice.

In some aspects, one integrates human $J_H2$ segment into mouse $J_H$ locus. The only conserved feature of CDR H3 for the VRC01 family is a W residue at position 100B (6), which can be provided by the human $J_H2$ segment. Because of high levels of mutation in VRC01 antibodies and the random nature of N-nucleotides, it is difficult to ascertain the authentic germline CDR H3 sequence, including the identity of the D segment. Therefore, we only integrated the human $J_H2$ segment into mouse $J_H^a$ locus; recombination of human $J_H2$ with mouse D segments creates diverse CDR H3's. Given the variable nature of CDR H3 of VRC01 family of antibodies (6), at least a fraction of the CDR H3 generated by this combination are compatible with the interaction of VRC01 with gp120. In addition, diverse CDR H3s permits the selection of antibodies that bind gp120, but do not cross-react with self-antigens and therefore will not be subject to developmental blocks via bone marrow tolerance mechanisms. We generated a targeting construct to replace the entire mouse $J_H1$-$J_H4$ region with human $J_H2$ (FIG. 1A, step 5). The targeting construct was introduced into the IGHV1-2*02/IGCRID/$J_H^b$DNRC01LC ES clone.

Certain mutations in Qa-1 have been shown to lead to abnormally large germinal centers in mice (7). We explored the incorporation of such Qa-1 mutations into the presently described system to see if it would accelerate affinity maturation. However, we were unable to find additional benefits from the mutation as we found that the frequency of somatic hypermutation is comparable between Qa-1 and control mice (data not shown). However, this does not exclude the option, that in some aspects additional mutations can be introduced to the system to enhance its function.

In some aspects, the invention provides a mouse model or mouse system for expressing the unmutated precursor of VRC01 antibody. To facilitate the incorporation of other human antibody genes into this system, an I-SceI cleavage site was introduced into the $V_H81X$ locus and a target sequence for a guide RNA of Cas9 into the Jk□ locus; the targeting construct for integrating the human $J_H2$ into the $J_H$ locus can also integrate a target site for a guide RNA of Cas9. Introduction of double strand breaks at these loci by I-SceI or Cas9 can increase the efficiency of gene targeting. The modified ES clones can be used with the RDBC approach to efficiently generate cohorts of chimeric mice. Moreover, all of the RDBC chimeric mice so far transmit their genetic modifications into the germline.

In certain aspects, the invention provides a mouse model expressing unmutated precursor of VRC01. We describe a mouse model expressing the unmutated precursor of VRC01 as well as mice that include the VRC01 Ig light chain and the human $J_H2$ segment. Also described herein are, e.g. ES cells, which incorporate the various affinity maturation intermediates of VRC01 (8).

Development of conditional expression system for BnAbs that are subject to negative control by tolerance mechanisms in the bone marrow. Some BnAbs are poly-reactive and can bind to self-antigens. As a result, B cells expressing these BnAbs in mice are subject to developmental blockage by tolerance mechanisms in bone marrow (9).

Figure 3:
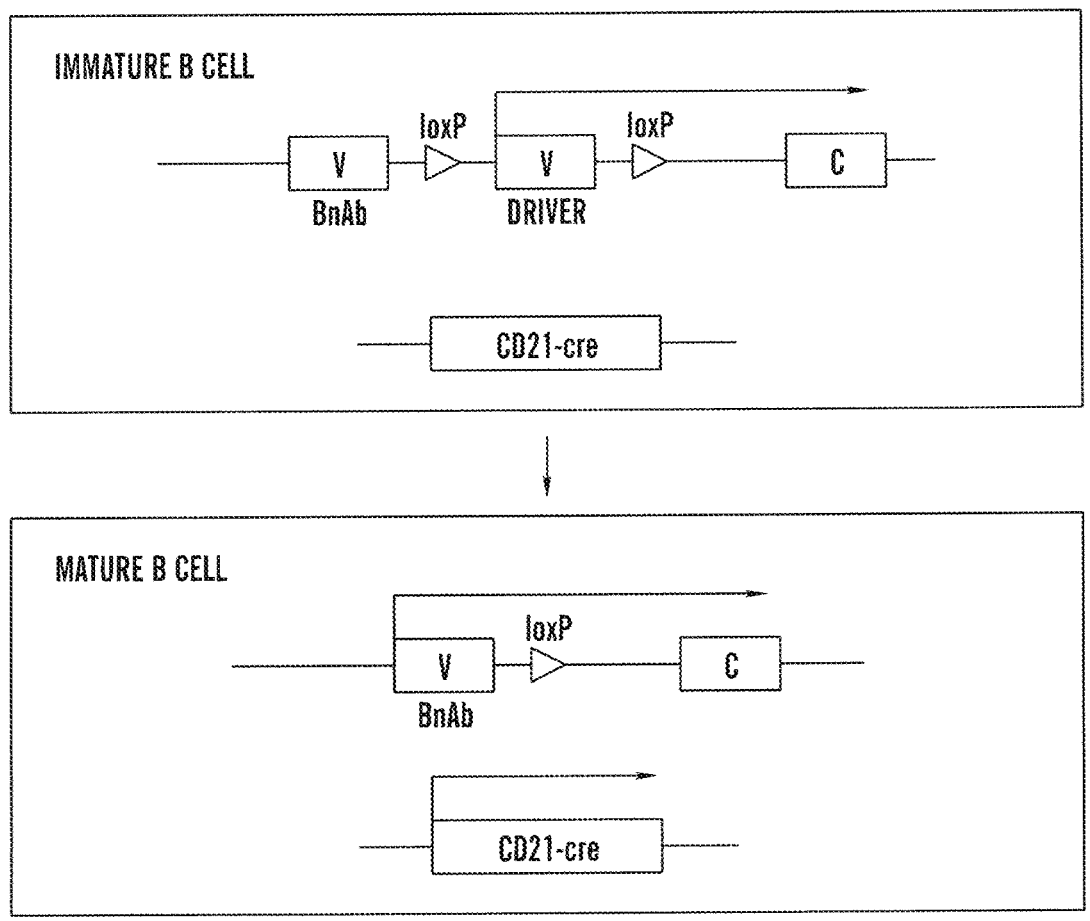
FIG. 3 depicts a schematic of conditional expression of antibodies, e.g. BnAbs.

To address this issue, in some aspects, we provide a system and a method to express BnAbs specifically in mature B cells, thereby circumventing tolerance mechanisms in the bone marrow. In this system or method, Ig variable region genes that encode non-self reactive antibodies in B cell precursors are expressed in bone marrow; these antibody genes are referred to herein as "driver V genes" (FIG. 3). The BnAb genes are positioned upstream of the driver V genes and will not be expressed in bone marrow. When these B cells have become mature B cells in peripheral lymphoid tissues, the driver V gene are deleted by flanking loxP sites by cre recombinase that is specifically expressed in mature B cell stage (CD21-cre, FIG. 3). As a result, the BnAb genes will replace the driver V gene and be expressed in mature B cells. This method or system can be used to express, e.g., BnAbs VRC26 (10) and DH270.

We derived an ES cell line from CD21-cre transgenic mice; so that we were able to construct the conditional expression to directly introduce into the CD21-cre ES cell line instead of relying on mouse breeding. Conditional expression constructs for VRC26 and DH270 were then constructed and transfected into CD21-cre ES cells.

Figure 4:
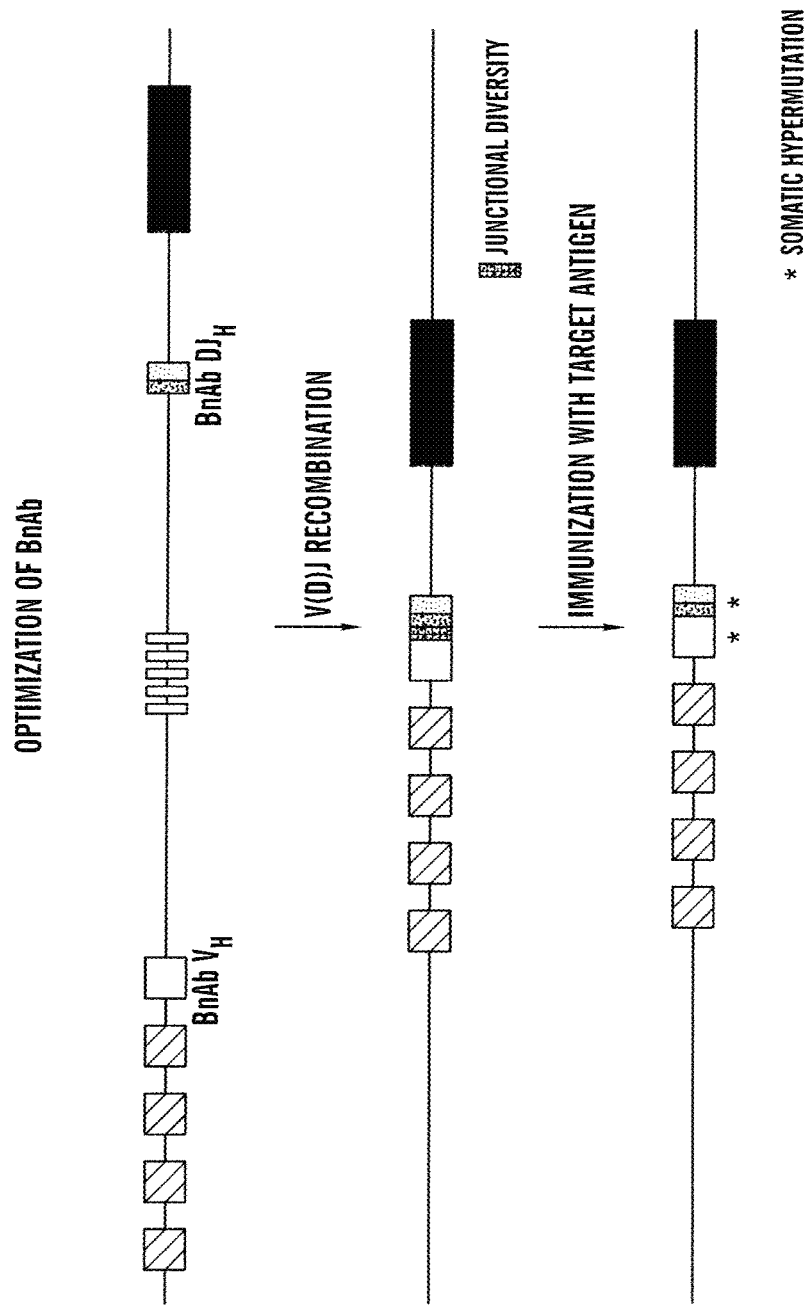
FIG. 4 depicts a schematic of antibody optimization, e.g. BnAb optimization.

In some aspects, the invention provides methods for optimization of BnAbs for treating HIV infection. One can adapt the above-described system, for example, to improve BnAbs for AIDS therapy as described herein. For this application the $V_H$ and $DJ_H$ segments of BnAbs are incorporated into the $V_H81X$ and $J_H$ loci respectively (FIG. 4). When the $V_H$ and $DJ_H$ segments are joined via V(D)J recombination during B cell development, junctional diversity greatly expands the range of CDR H3, essentially creating a library of related antibodies with subtle differences in antigen binding site. Immunization with target antigen selects out B cells expressing high affinity antibodies, which can be further optimized through somatic hypermutation. In some embodiments, the BnAbs can be DH270 or CH103 (11). The mature DH270 antibody contains relatively low levels of somatic hypermutation, potentially leaving more room for further optimization by additional rounds of affinity maturation. The mutation frequency of CH103 antibody is also lower than that reported for VRC01, and does not exhibit as broad a range of neutralization activity as some of the other BnAbs. For both DH270 and CH103, CDR H3 constitutes an important part of the interface with HIV envelope protein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the term "activator," as used in reference to activation of B cells refers to an antigen that increases B cell activation, e.g. increases B cell proliferation, SHM, and/or the GC reaction.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

In another example, an antibody includes two heavy (H) chain variable regions and two light (L) chain variable regions. It should be noted that a $V_H$ region (e.g. a portion of an immunglobin polypeptide is not the same as a $V_H$ segment, which is described elsewhere herein). The $V_H$ and $V_L$ regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each $V_H$ and $V_L$ is typically composed of three CDRs and four FRs, arranged from amino-terminus to carboxy-terminus in the following order: FR1, CDR1, FR2, CDR2, FR3, CDR3, FR4.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

As described herein, an "antigen" is a molecule that is bound by a binding site on an antibody. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "affinity" refers to the strength of an interaction, e.g. the binding of an antibody for an antigen and can be expressed quantitatively as a dissociation constant ($K_D$). Avidity is the measure of the strength of binding between an antigen-binding molecule (such as an antibody reagent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody reagent described herein) will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$. Preferably, a binding site on an antibody reagent described herein will bind to the desired antigen with an affinity less than 500 nM, preferably less than 200 nM, more preferably less than 10 nM, such as less than 500 pM. Specific binding of an antibody reagent to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

As used herein, the term "specific binding" or "specificity" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. Accordingly, as used herein, "selectively binds" or "specifically binds" refers to the ability of an agent (e.g. an antibody reagent) described herein to bind to a target, such a peptide comprising, e.g. the amino acid sequence of a given antigen, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if an agent described herein binds to a first peptide comprising the antigen with a $K_D$ of $10^{-5}$ M or lower, but not to another randomly selected peptide, then the agent is said to specifically bind the first peptide. Specific binding can be influenced by, for example, the affinity and avidity of the agent and the concentration of the agent. The person of ordinary skill in the art can determine appropriate conditions under which an agent selectively bind the targets using any suitable methods, such as titration of an agent in a suitable cell and/or a peptide binding assay.

As used herein, the term "chimeric", as used in the context of an antibody, or sequence encoding an antibody refers to immunoglobin molecules characterized by two or more segments or portions derived from different animal species. For example, the variable region of the chimeric antibody is derived from a non-human mammalian antibody, such as murine monoclonal antibody, and the immunoglobin constant region is derived from a human immunoglobin molecule. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted. Techniques developed for the production of "chimeric antibodies" are known in the art (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties), e.g., by splicing genes from a mouse, or other species, antibody molecule of appropriate antigen specificity together with genes from a human antibody molecule of appropriate biological activity.

As used herein, the term "humanized" refers to an antibody (or fragment thereof, e.g. a light or heavy chain) wherein the CDRs are not human in origin, but the sequence of the remaining sequence of the Ig protein (e.g. the framework regions and constant regions) is human in origin. One of skill in the art is aware of how to humanize a given antibody, see, e.g., U.S. Pat. Nos. 5,585,089; 6,835,823; 6,824,989.

As used herein, the term "engineered" refers to the aspect of having been manipulated by the hand of man. For example, a locus is considered to be "engineered" when two or more sequences, that are not linked together in that order in nature in that locus, are manipulated by the hand of man to be directly linked to one another in the engineered locus. For example, in some embodiments of the present invention, an engineered locus comprises various IgH sequences with a non-native $V_H$ segment, all of which are found in nature, but are not found in the same locus or are not found in that order in the locus in nature. As is common practice and is understood by those in the art, progeny and copies of an engineered polynucleotide (and/or cells or animals comprising such polynucleotides) are typically still referred to as "engineered" even though the actual manipulation was performed on a prior entity.

As used herein, the term "recombination-defective" refers to a cell (or animal) in which recombination, particularly V(D)J recombination at the IgH and IgL loci cannot occur. Typically, a V(D)J recombination-defective cell is a cell comprising a mutation in a gene encoding a protein that is necessary for V(D)J recombination to occur. Mutations that will cause a cell and/or animal to be V(D)J recombination-defective are known in the art, e.g., $RAG2^{-/-}$ cells are V(D)J recombination defective and mice with such mutations are commercially available (see, e.g., stock number 008449, Jackson Laboratories, Bar Harbor, ME). A further non-limiting example of a V(D)J recombination-defective mutant is $RAG1^{-/-}$. In some embodiments, cells can be rendered V(D)J recombination-defective at only one locus, e.g. the IgH locus by, e.g. deleting the germline $J_H$ segments.

As used herein, the term "cassette" refers to a nucleic acid molecule, or a fragment thereof, that can be introduced to a host cell and incorporated into the host cell's genome (e.g. using a cassette-targeting sequence as described elsewhere herein). A cassette can comprise a gene (e.g. an IgH gene), or a fragment thereof, e.g. a $V_H$ segment. A cassette can be an isolated nucleotide fragment, e.g. a dsDNA or can be comprised by a vector, e.g. a plasmid, cosmid, and/or viral vector.

As used herein, the term "B cell" refers to lymphocytes that play a role in the humoral immune response and is a component of the adaptive immune system. In this application the expressions "B cell", "B-cell" and "B lymphocyte" refer to the same cell.

Immature B cells are produced in the bone marrow of most mammals. After reaching the IgM+ immature stage in the bone marrow, these immature B cells migrate to lymphoid organs, where they are referred to as transitional B cells, some of which subsequently differentiating into mature B lymphocytes. B-cell development occurs through several stages, each stage characterized by a change in the genome content at the antibody loci.

Each B cell has a unique receptor protein (referred to as the B-cell receptor (BCR)) on its surface that is able to bind to a unique antigen. The BCR is a membrane-bound immunoglobulin, and it is this molecule that allows to distinguish B cells from other types of lymphocytes, as well as playing a central role in B-cell activation in vivo. Once a B cell encounters its cognate antigen and receives an additional signal from a T helper cell, it can further differentiate into one of two types of B cells (plasma B cells and memory B cells). The B cell may either become one of these cell types directly or it may undergo an intermediate differentiation step, the germinal center reaction, during which the B cell hypermutates the variable region of its immunoglobulin gene ("somatic hypermutation") and possibly undergoes class switching.

Plasma B cells (also known as plasma cells) are large B cells that have been exposed to an antigen and are producing and secreting large amounts of antibodies. These are short-lived cells and usually undergo apoptosis when the agent that induced the immune response is eliminated. Memory B cells are formed from activated B cells that are specific to an antigen encountered during a primary immune response. These cells are able to live for a long time, and can respond quickly following a second exposure to the same antigen.

As used herein, the term "GC reaction" refers to a process that occurs in the germinal center, during which B cells undergo SHM, memory generation, and/or class/isotype switch. The germinal center (GC) reaction is the basis of T-dependent Immoral immunity against foreign pathogens and the ultimate expression of the adaptive immune response. GCs represent a unique collaboration between proliferating antigen-specific B cells, T follicular helper cells, and the specialized follicular dendritic cells that constitutively occupy the central follicular zones of secondary lymphoid organs.

As used herein, the term "somatic hypermutation" or "SHM," refers to the mutation of a polynucleotide sequence at an Ig locus initiated by, or associated with the action of AID (activation-induced cytidine deaminase) on that polynucleotide sequence. SHM occurs during B cell proliferation and occurs at a mutation rate that is at least $10^5$-$10^6$ fold greater than the normal rate of mutation in the genome.

As used herein, the term "stem cell" refers to a cell in an undifferentiated or partially differentiated state that has the property of self-renewal and has the developmental potential to naturally differentiate into a more differentiated cell type, without a specific implied meaning regarding developmental potential (i.e., totipotent, pluripotent, multipotent, etc.). By self-renewal is meant that a stem cell is capable of proliferation and giving rise to more such stem cells, while maintaining its developmental potential. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. The term "somatic stem cell" is used herein to refer to any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells and hematopoietic stem cells. In some embodiments, the stem or progenitor cells can be embryonic stem cells. As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are totipotent cells derived from the early embryo or blastocyst. Embryonic stem cells can be obtained directly from suitable tissue, including, but not limited to human tissue, or from established embryonic cell lines. In one embodiment, embryonic stem cells are obtained as described by Thomson et al. (U.S. Pat. Nos. 5,843,780 and 6,200,806; Science 282:1145, 1998; Curr. Top. Dev. Biol. 38:133 ff, 1998; Proc. Natl. Acad. Sci. U.S.A. 92:7844, 1995 which are incorporated by reference herein in their entirety).

Exemplary stem cells include embryonic stem cells, adult stem cells, pluripotent stem cells, bone marrow stem cells, hematopoietic stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25):14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735. Descriptions of stromal cells, including methods for isolating them, may be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A cell comprising an engineered IgH locus in which the 3'-most $V_H$ segment of the IgH locus is engineered to comprise a cassette targeting sequence.
2. The cell of paragraph 1, wherein the cassette targeting sequence permits the replacement of the 3'-most $V_H$ segment.
3. The cell of paragraph 1, wherein the cassette targeting sequence is selected from the group consisting of:
   an I-SceI meganuclease site; a Cas9/CRISPR target sequence; a Talen target sequence or a recombinase-mediated cassette exchange system.
4. The cell of any of paragraphs 1-3, wherein the 3'-most $V_H$ segment of the IgH locus has been engineered to comprise a non-native $V_H$ segment sequence.
5. The cell of paragraph 4, wherein the IgH locus is a mouse locus and the 3'-most $V_H$ segment of the IgH locus has been engineered to comprise any $V_H$ segment other than the original mouse 3'-most $V_H$ segment.
6. The cell of any one of the paragraphs 1-5, wherein the cell is a mouse embryonic stem cell.
7. The cell of any one of the paragraphs 4-6, wherein the non-native $V_H$ segment is a human $V_H$ segment.
8. The cell of paragraph 1, wherein the non-native $V_H$ segment is a $V_H$ segment from a known antibody in need of improvement of affinity or specificity.
9. The cell of paragraph 8, wherein the non-native $V_H$ segment is a human $V_H$ segment from a known antibody in need of improvement of affinity or specificity.
10. The cell of paragraph 9, wherein the human $V_H$ segment is IGHV1-2*02, IGV$_H$1-46 or IGHV1-69.
11. The cell of any one of paragraphs 1-10, further comprising a non-functional IGCR1 sequence within the nucleic acid sequence separating the 3' end of the 3'-most $V_H$ segment and the 5' end of a $D_H$ segment.
12. The cell of paragraph 11, wherein the non-functional IGCR1 sequence comprises mutated CBE sequences.
13. The cell of paragraph 11, wherein the CBE sequences of the IGCR1 sequence have been deleted.
14. The cell of paragraph 11, wherein the IGCR1 sequence has been deleted from the IgH locus.
15. The cell of any of paragraphs 1-14, further comprising:
   a 3' recombinase site being located 3' of the one or more $J_H$ segments;
   and a passenger cassette being located at the position of a deleted native 3'-most $V_H$ segment, the passenger cassette comprising, from 5' to 3':
   a 5' recombinase site
   an inverted passenger VDJ exon and/or a cassette targeting sequence; and
   a maturation-compatible $V_H$ segment;
   wherein the recombinase sites are inverted with respect to each other.

16. The cell of any of paragraphs 1-14, wherein the locus further comprises:
   a 3' recombinase site being located 3' of the one or more $J_H$ segments;
   and a passenger cassette being located at the position of a deleted native 3'-most $V_H$ segment, the passenger cassette comprising, from 5' to 3':
      a 5' to 3'-oriented passenger VDJ exon and/or a cassette targeting sequence;
      a 5' recombinase site; and
      a maturation-compatible $V_H$ segment;
      wherein the recombinase sites are in the same orientation.
17. The cell of any of paragraphs 15-16, wherein the recombinase site is a LoxP site and the cell further comprises a locus encoding cre recombinase.
18. The engineered cell of paragraph 17, wherein the locus encoding cre recombinase is under the control of a promoter which is not active in immature B cells and is active in peripheral B cells.
19. The cell of paragraph 18, wherein the promoter is the CD21 promoter.
20. The cell of any of paragraphs 1-19, wherein one or more $D_H$, one or more $J_H$ segments, and/or a $DJ_H$ fusion comprise a cassette targeting sequence.
21. The cell of any of paragraphs 1-20, wherein the IgH locus comprises one or more non-native $D_H$ segments.
22. The cell of any of paragraphs 1-21, wherein the IgH locus comprises one $D_H$ segment.
23. The cell of any of paragraphs 1-22, wherein the IgH locus comprises one or more non-native $J_H$ segments.
24. The cell of paragraph 23, wherein the $J_H$ segment is human $J_H2$.
25. The cell of any of paragraphs 1-24, wherein the IgH locus comprises one $J_H$ segment.
26. The cell of any of paragraphs 1-25, wherein the IgH locus comprises murine IgH locus sequence.
27. The cell of any of paragraphs 1-26 wherein the IgH locus comprises human IgH locus sequence.
28. The cell of any of paragraphs 1-27, wherein the locus comprises humanized IgH locus sequence.
29. The cell of any of paragraphs 1-28, wherein the $J_H$ locus has been replaced by human D and $J_H$ cassette or a cassette with an assembled human $DJ_H$.
30. The cell of any of paragraphs 1-29, wherein the cell is heterozygous for the engineered IgH locus of any of paragraphs 1-29 and the other IgH locus has been engineered to be inactive, wherein the cell will express an IgH chain only from the engineered IgH locus of any of paragraphs 1-29.
31. The cell of any of paragraphs 1-30, further comprising an IgL locus with human sequence.
32. The cell of any of paragraphs 1-31, further comprising a humanized IgL locus.
33. The cell of any of paragraphs 1-32, further comprising a human IgL locus.
34. The cell of any of paragraphs 1-33, further comprising an IgL locus with one $V_L$ segment.
35. The cell of any of paragraphs 1-34, further comprising an IgL locus with one $J_L$ segment.
36. The cell of any of paragraphs 1-35, further comprising a human rearranged $V_L J_L$ at the IgL kappa or lambda locus.
37. The cell of any of paragraphs 1-36, further comprising a human rearranged $V_L J_L$ at the murine IgL kappa or lambda locus.
38. The cell of any of paragraphs 31-37, wherein the IgL locus encodes IGκV1 or VRC01 IgL.
39. The cell of any of paragraphs 1-38, wherein the cell is a stem cell or an embryonic stem cell.
40. The cell of any of paragraphs 1-39, wherein the cell is a murine cell.
41. The cell of any of paragraphs 1-40, further comprising a mutation capable of activating, inactivating or modifying genes that in a lymphocyte-intrinsic fashion lead to increased GC antibody maturation responses.
42. A cell comprising an engineered IgH locus, wherein the 3'-most $V_H$ segment has been replaced with a non-native $V_H$ segment.
43. The cell of paragraph 42, wherein the IgH locus is a mouse locus and the 3'-most $V_H$ segment of the IgH locus has been engineered to comprise any $V_H$ segment other than the original mouse 3'-most $V_H$ segment.
44. The cell of any one of the paragraphs 42-43, wherein the cell is a mouse embryonic stem cell.
45. The cell of any one of the paragraphs 42-44, wherein the non-native $V_H$ segment is a human $V_H$ segment.
46. The cell of paragraph 42-45, wherein the non-native $V_H$ segment is a $V_H$ segment from a known antibody in need of improvement of affinity or specificity.
47. The cell of paragraph 46, wherein the non-native $V_H$ segment is a human $V_H$ segment from a known antibody in need of improvement of affinity or specificity.
48. The cell of paragraph 47, wherein the human $V_H$ segment is IGHV1-2*02, $IGV_H$1-46 or IGHV1-69.
49. The cell of any one of paragraphs 42-48, further comprising a non-functional IGCR1 sequence within the nucleic acid sequence separating the 3' end of the 3'-most $V_H$ segment and the 5' end of a $D_H$ segment.
50. The cell of paragraph 49, wherein the non-functional IGCR1 sequence comprises mutated CBE sequences.
51. The cell of paragraph 49, wherein the CBE sequences of the IGCR1 sequence have been deleted.
52. The cell of paragraph 49, wherein the IGCR1 sequence has been deleted from the IgH locus.
53. The cell of any of paragraphs 42-52, further comprising:
   a 3' recombinase site being located 3' of the one or more $J_H$ segments;
   and a passenger cassette being located at the position of a deleted native 3'-most $V_H$ segment, the passenger cassette comprising, from 5' to 3':
      a 5' recombinase site
      an inverted passenger VDJ exon and/or a cassette targeting sequence; and
      a maturation-compatible $V_H$ segment;
   wherein the recombinase sites are inverted with respect to each other.
54. The cell of any of paragraphs 42-52, wherein the locus further comprises:
   a 3' recombinase site being located 3' of the one or more $J_H$ segments;
   and a passenger cassette being located at the position of a deleted native 3'-most $V_H$ segment, the passenger cassette comprising, from 5' to 3':
      a 5' to 3'-oriented passenger VDJ exon and/or a cassette targeting sequence;
      a 5' recombinase site; and
      a maturation-compatible $V_H$ segment;
      wherein the recombinase sites are in the same orientation.

55. The cell of any of paragraphs 53-54, wherein the recombinase site is a LoxP site and the cell further comprises a locus encoding cre recombinase.
56. The engineered cell of paragraph 55, wherein the locus encoding cre recombinase is under the control of a promoter which is not active in immature B cells and is active in peripheral B cells.
57. The cell of paragraph 56, wherein the promoter is the CD21 promoter.
58. The cell of any of paragraphs 42-57, wherein one or more $D_H$, one or more $J_H$ segments, and/or a $DJ_H$ fusion comprise a cassette targeting sequence.
59. The cell of any of paragraphs 42-58, wherein the IgH locus comprises one or more non-native $D_H$ segments.
60. The cell of any of paragraphs 42-59, wherein the IgH locus comprises one $D_H$ segment.
61. The cell of any of paragraphs 42-60, wherein the IgH locus comprises one or more non-native $J_H$ segments.
62. The cell of paragraph 61, wherein the $J_H$ segment is human $J_H2$.
63. The cell of any of paragraphs 42-62, wherein the IgH locus comprises one $J_H$ segment.
64. The cell of any of paragraphs 42-63, wherein the IgH locus comprises murine IgH locus sequence.
65. The cell of any of paragraphs 42-63, wherein the IgH locus comprises human IgH locus sequence.
66. The cell of any of paragraphs 42-63, wherein the locus comprises humanized IgH locus sequence.
67. The cell of any of paragraphs 42-66, wherein the $J_H$ locus has been replaced by human D and $J_H$ cassette or a cassette with an assembled human $DJ_H$.
68. The cell of any of paragraphs 42-67, wherein the cell is heterozygous for the engineered IgH locus of any of paragraphs 42-67 and the other IgH locus has been engineered to be inactive, wherein the cell will express an IgH chain only from the engineered IgH locus of any of paragraphs 42-67.
69. The cell of any of paragraphs 42-68, further comprising an IgL locus with human sequence.
70. The cell of any of paragraphs 42-69, further comprising a humanized IgL locus.
71. The cell of any of paragraphs 42-70, further comprising a human IgL locus.
72. The cell of any of paragraphs 42-71, further comprising an IgL locus with one $V_L$ segment.
73. The cell of any of paragraphs 42-72, further comprising an IgL locus with one $J_L$ segment.
74. The cell of any of paragraphs 42-73, further comprising a human rearranged $V_L J_L$ at the IgL kappa or lambda locus.
75. The cell of any of paragraphs 42-74, further comprising a human rearranged $V_L J_L$ at the murine IgL kappa or lambda locus.
76. The cell of any of paragraphs 42-75, wherein the IgL locus encodes ION' or VRC01 IgL.
77. The cell of any of paragraphs 42-76, wherein the cell is a stem cell or an embryonic stem cell.
78. The cell of any of paragraphs 42-77, wherein the cell is a murine cell.
79. The cell of any of paragraphs 42-78, further comprising a mutation capable of activating, inactivating or modifying genes that in a lymphocyte-intrinsic fashion lead to increased GC antibody maturation responses.
80. A genetically engineered mouse comprising the cell of any of paragraphs 1-79.
81. A chimeric genetically engineered mouse comprising two populations of cells,
a first population comprising cells which are V(D)J recombination-defective; and
a second population comprising cells of any of paragraphs 1-79.
82. The mouse of paragraph 81, wherein the V(D)J recombination-defective cells are $RAG2^{-/-}$ cells.
83. The mouse of any of paragraphs 80-82, wherein the mammal is a mouse.
84. A method of making an optimized antibody from a known antibody, the method comprising the steps of:
injecting a mouse blastocyst with a cell of any of the paragraphs 1-79, wherein the cell is a mouse embryonic stem cell, and wherein the $V_H$ segment comprises the $V_H$ segment of the known antibody at the position of the native 3'most $V_H$ segment;
implanting the mouse blastocyst into a female mouse under conditions suitable to allow maturation of the blastocyst into a genetically engineered mouse;
isolating
1) an optimized antibody comprising the non-native $V_H$ segment; or
2) a cell producing an optimized antibody comprising the non-native $V_H$ segment from the genetically engineered mouse.
85. The method of paragraph 84, further comprising a step of immunizing the genetically engineered mouse with a desired target antigen before the isolating step.
86. The method of any of paragraphs 84-85, further comprising a step of producing a monoclonal antibody from at least one cell of the genetically engineered mouse.
87. The method of any of paragraphs 84-86, wherein the IgH locus of the embryonic stem cell comprises a pre-rearranged $DJ_H$ segment from the known antibody.
88. The method of any of paragraphs 84-87, wherein the IgL locus of the embryonic stem cell comprises a pre-arranged light chain sequence from the known antibody.
89. The method of any of paragraphs 84-88, wherein the $V_H$ segment of interest is a germline $V_H$ segment, an affinity maturation intermediate, or a mature $V_H$ segment.
90. An optimized antibody produced by any one of the methods of paragraphs 84-89.
91. A method of producing B lymphocytes comprising $V_H(D)J_H$ rearrangements with a $V_H$ segment from a known monoclonal antibody, the method comprising the steps of:
engineering a mouse embryonic stem cell by replacing the most proximal $V_H$ segment of a mouse IgH locus with the $V_H$ segment from a known monoclonal antibody;
and injecting the engineered mouse embryonic stem cells into a blastocyst of a mouse which is incapable of forming mature B cells, thereby creating a chimeric mouse that produces B lymphocytes comprising $V_H(D)J_H$ rearrangements comprising the $V_H$ segment from the known monoclonal antibody.
92. The method of paragraph 91, wherein the cells of the blastocyst are V(D)J recombination-defective cells.
93. The method of paragraph 92, wherein the cells of the blastocyst are $RAG2^{-/-}$ cells.
94. The method of paragraph 91, wherein the cells of the blastocyst are not capable of forming mature lymphocytes.
95. The method of any of paragraphs 91-94, further comprising engineering the mouse embryonic stem cell to destroy functionality of the IGCR1 sequence in the nucleic acid sequence separating the 3' end of the most proximal $V_H$ segment.
96. The method of any one of paragraphs 91-95, wherein the engineered cell further comprises IgL sequence from the known monoclonal antibody.

97. The method of any one of paragraphs 91-96, wherein the engineered cell further comprises a $J_H$ locus that has been replaced by a human D and $J_H$ cassette or a cassette with an assembled human $DJ_H$.

98. The method of any of paragraphs 91-97, further comprising a step of breeding the chimeric mouse to produce a mouse that harbors a germline $V_H$ segment from the known antibody.

99. The method of any of paragraphs 91-98, wherein the ES cell is made homozygous for the human $V_H$ segment.

100. The method of any one of paragraphs 91-99, wherein the human $V_H$ segment consists essentially of a sequence of a $V_H$ segment from a known monoclonal antibody.

101. A method of identifying a candidate antigen as an antigen that activates a B cell population comprising a $V_H$ segment of interest, the method comprising:
immunizing a mammal of paragraphs 80-83, engineered such that a majority of the mammal's peripheral B cells express the $V_H$ segment of interest, with the antigen;
measuring B cell activation in the mammal; and
identifying the candidate antigen as an activator of a B cell population comprising the $V_H$ segment of interest if the B cell activation in the mammal is increased relative to a reference level.

102. The method of paragraph 101, wherein an increase in B cell activation is an increase in the somatic hypermutation status of the Ig variable region.

103. The method of paragraph 101, wherein an increase in B cell activation is an increase in the affinity of mature antibodies for the antigen.

104. The method of paragraph 101, wherein an increase in B cell activation is an increase in the specificity of mature antibodies for the antigen.

105. The method of any of paragraphs 101-104, wherein the $V_H$ segment of interest is a germline $V_H$ segment, an affinity maturation intermediate, or a mature $V_H$ segment.

EXAMPLES

Example 1

The following examples are provided herein as exemplary embodiments and are not to be construed to limit the scope of the invention, which is defined by the claims.

Humanized antibodies have now become a major line of therapeutics for a broad set of diseases ranging from autoimmunity to cancer (1). They are also under development for management of HIV infection (2). Human monoclonal antibodies have been derived from many different approaches including phage display, immunization of mice containing humanized immunoglobulin (Ig) loci (1), and, for example in the case of HIV, cloning antibody variable region genes from single cells of infected patients that produce broadly neutralizing antibodies (3). While such human or humanized antibodies have been extremely effective therapeutically, the ability to readily generate variants of these antibodies with higher affinities or modified specificities via in vivo immunization strategies would be highly desirable, both in the context of generating more effective antibody therapeutics and also for elucidating potential vaccine strategies for eliciting antibody production in patients. We describe here a novel approach, based on a number of technical advances from our lab, for the generation of "high throughput" antibody producing mouse models that could achieve the goals outlined above.

Diversification of Primary and Secondary (Affinity Matured) Antibody Repertoires The antigen receptor of B lymphocytes is comprised of a pair of identical Ig heavy (IgH) and light (IgL) chains. The secreted form of this complex is an antibody. The variable regions of IgH and IgL chains form the antigen-binding site, whereas the constant region of IgH chain mediates effector functions of antibodies. The exons that encode the IgH and IgL variable regions are assembled from $V_H$, D, $J_H$ and $V_L$, $J_L$ gene segments respectively via V(D)J recombination reaction that occurs during B cell maturation in adult bone marrow (4). Diversification of primary antibody repertoires is contributed largely by V(D)J recombination. Thus, counting only the functional gene segments, there are 39 $V_H$, $25D_H$ and $6J_H$ segments in the human IgH locus, and the two IgL loci (K and X) are of comparable complexity (5). Assembly of these different combinations of V, D and J segments in different assortments give rise to a large number of distinct antigen-binding sites, as each germline V segment contains two different encoded antigen contact regions ("CDR1" and "CDR2"). Moreover, the $V_H(D)J_H$ or $V_LJ_L$ junctional region encodes a third CDR (CDR3) that is generated somatically by V(D)J recombination. CDR3 can have tremendous diversity because nucleotides can both be deleted and added (in a non-templated fashion) to $V_HD$ and $DJ_H$ junctions in the case of IgH or to $V_LJ_L$ junctions in humans, further increasing the complexity of CDR3 in variable regions and, correspondingly, the ability of the body to produce a huge number of B cells that each produce a unique BCR specificity. The association of different IgH and IgL chains adds another layer of diversity to antibody repertoire. Upon completion of IgH and IgL variable region exon assembly in developing bone marrow B cells, the two chains are expressed as a B cell receptor (BCR) and the resulting B lymphocytes migrate out of bone marrow and circulate in various lymphoid tissues, where individual B cells can be exposed to antigens from pathogens that bind to their BCR, leading to their activation to secrete antibodies and also to potentially undergo additional genomic alterations that can lead to further diversification/affinity maturation of their BCRs/antibodies. During the course of their development, a significant fraction of developing B cells are lost due to poor pairing of their assembled IgH and IgL chains, auto-reactivity of the paired IgH and IgL chains, and other related factors. However, within the huge primary B cell population that does move on to become functional peripheral B cells, there is a sufficient diversity of BCRs to allow at least some B cells to recognize any of the vast diversity of different antigens that might be encountered.

Binding of antigen to B cell receptors in peripheral lymphoid organs activates B cells to undergo IgH class switch recombination (CSR) and IgH and IgL variable region exon somatic hypermutation (6, 7). Class switch recombination enables B cells to produce different classes of antibodies such as IgM, IgG, IgA and IgE, which contain different IgH constant regions that mediate distinct effector functions. Somatic hypermutation alters the sequences of IgH and IgL variable region exons in the context of the germinal center (GC) reaction, which allows the body to select for B cells with SHMs in their variable region exons that generate higher affinity antigen-binding BCRs and secreted antibodies. This general process is referred to as antibody affinity maturation. B cells with SHMs that are neutral or have a negative effect on BCR affinity are generally lost during the GC reaction. Eventually, B cells that are capable of producing higher affinity antibodies differentiate into memory B cells and long-lived plasma cells, which confer long-term protection against future infections. Although CSR can be recapitulated under in vitro B cell activation conditions, neither SHM nor the GC reaction has been reproduced in vitro.

Generation of Therapeutic Antibodies with Increased Affinities and/or Altered Specificities The efficacy of an antibody depends upon its specificity and affinity toward a relevant antigen; as described above, both V(D)J recombination and SHM make important contributions in this respect but at different points in the evolution of the antibody. V(D)J recombination creates an enormous pool of antigen-binding sites so that any potential antigen might find a reasonable match; once a matched B cell has been found, somatic hypermutation and the GC response fine-tune the antigen-binding site to perfect the antibody-antigen interaction. We propose to utilize the power of V(D)J recombination and, in particular, somatic hypermutation to optimize known antibodies for therapeutic applications or to design approaches to generate desired mono-clonal antibodies from known intermediates.

Until now, V(D)J rearrangements harboring desired human $V_HDJ_H$ or $V_LJ_L$ exons have been obtained by inactivating the V(D)J portion of the mouse IgH or IgL locus and generating mice containing either a portion of or the entire V, D, and J segment of the human IgH or IgL locus to force the mice to use human V, D, and J segments to produce their antibodies (8). This approach is clearly desirable to make new antibodies against most novel antigens as it exploits the ability to make mice with a large primary B cell repertoire that employs de novo assembled human IgH and IgL V(D)J exons. Such mice can then be immunized to select out and affinity mature in vivo the rare B cells clones that bind the test antigen. While extremely effective, many antibodies generated in this fashion, or by other methods such as phage display, may not have the optimal possible binding efficiency or affinity for a given therapeutic approach. Therefore, an in vivo method to further enhance or alter the binding specificities of human monoclonal antibodies for which rearranged IgH and IgL V(D)J exon sequences are known would be desirable. Based on several approaches developed in our lab along with several recent findings from our lab, we are generating a rapid and efficient approach to achieve this goal.

This in vivo antibody affinity maturation approach will be based upon the use of the RAG-2 deficient blastocyst complementation (RDBC) method that was developed by our lab two decades ago as a method to generate chimeric mice in which all mature B (and T) lymphocytes are generated from ES cells that harbor targeted alterations of their genome (9). The basic approach is to modify an ES cell in a desired manner and then to inject the modified ES cells into blastocysts from RAG-2-deficient mice. These ES cell injected blastocysts are then implanted into foster mothers to generate offspring whose somatic tissues generally have representation from both the injected ES cell-derived and blastocyst-derived cell lineages. However, as RAG-2 is essential for V(D)J recombination, all B and T lymphocytes in such chimeras derive from the injected RAG-sufficient ES cells. This approach quickly and efficiently allows the generation of large numbers of chimeric mice in which all mature lymphocytes in the immune system derive from a genetically modified ES cell, an approach that avoids the time and expense of germline transmission. However, germline transmission, if desired, can be achieved by breeding the RDBC chimeras. Our lab has routinely used the approach to generate mice with all of their mature B and T cells being derived from mutant ES cells, including ES cells with various modifications of their antigen receptor loci.

The mouse IgH locus spans nearly 3 megabases (MB) with about 100 functional $V_H$ segments spread through several MB on the distal end followed by a 100 kb interval and then the 13 D segments embedded within an approximately 80 kb region immediately followed 1 kb downstream by 4 $J_H$ segments in a 1 kb region (10). The exons that encode the IgH constant regions ("$C_H$s") are embedded within a 200 kb region downstream of the $J_H$ region. The complete V(D)J exon is assembled at the $J_H$ locus with D to $J_H$ rearrangements occurring first to generate $DJ_H$ intermediates and then $V_H$ segments being appended to the $DJ_H$ intermediate to create the V(D)J exon. Transcription from a promoter upstream of the $V_H(D)J_H$ exon runs through the IgH constant region exons and RNA splicing appends the $V_H(D)J_H$ to the $C_H$ in the form of a mature $V_H(D)J_HC_H$ mRNA.

While all of the $V_H$ segments normally are utilized in developing B lymphocytes to generate a fully representative $V_H(D)J_H$ repertoire, we found that the most proximal $V_H$ segment ($V_H81X$) is utilized extremely frequently to generate primary $V_H(D)J_H$ rearrangements (11). However, $V_H8$ IX rarely contributes to productive (expressed) $V_H(D)J_H$ rearrangements; since it has difficulty pairing with surrogate IgL chains (which is necessary for early B cell development) and with IgL chains and also tends to encode auto-reactive antibodies (12). However, we speculated that any $V_H$ inserted in place of $V_H81X$ would also rearrange frequently and, correspondingly, be highly represented in primary IgH V(D)J repertoires if it did not undergo counter-selection like $V_H81X$. To test this notion, we replaced $V_H81X$ on one allele in mouse ES cells ("test ES cells") with a human $V_H$ segment, $IGV_H1-2*02$, and used those cells for RDBC. In the resulting chimeras, the rearrangements using $IGV_H1-2*02$ were substantially represented (i.e. comprised 4% or more of $V_H(D)J_H$ rearrangements based on analysis of hybridomas derived from splenic B cells) in peripheral B cell antibody repertoires.

Because of the addition of random nucleotides to $V_H$-$D_H$ and $D_H$-$J_H$ joints, the rearranged V(D)J region may contain an open reading frame and productively encode an IgH chain or may be out of frame and not encode an IgH chain (i.e. "non-productive"). Due to counter-selection at the cellular level of productive $V_H81X$ rearrangements, $V_H81X$ mostly appears in the periphery as non-productive rearrangements (13, 14). However, we found that about 70% of $V_H(D)J_H$ rearrangements involving $IGV_H1-2*02$ among peripheral mature B cells were productive, suggesting that this human $V_H$ segment can be functionally expressed in association with mouse $D_H$, $J_H$, and with mouse IgL; moreover, the B cells incorporating $IGV_H1-2*02$ as part of their BCR were not subject to negative selection during their maturation process. In addition, B cells harboring such $IGV_H1-2*02DJ_H$ BCRs underwent SHM at a frequency of about $1\times10^{-2}$ per base pair in the $IGV_H1-2*02$ segment of the rearrangement following immunization of the chimeras with sheep red blood cells. These findings provide proof-of-principle evidence that we can replace $V_H81X$ in a mouse IgH locus with a human $V_H$ and have it productively participate in $V_H(D)J_H$ rearrangements that generate peripheral B cells that can participate in an immune response and undergo SHM. We have also bred the RDBC chimeras and to establish a mouse line that harbors a germline $IGV_H1\text{-}2^*02$ segment replacement, demonstrating our ability to move genetic alterations of interest as established by RDBC into the germline for further studies or for sending out to collaborators.

We have recently discovered a mouse IgH locus V(D)J recombination regulatory region, termed intergenic control region 1 (IGCR-1), that lies just upstream of the most distal ($V_H$-proximal) D segment (15). This 4 kb IGCR-1 region relies on the integrity of two CTCF binding elements each about 18 bp long (CBEs) for its function and its activity can be inactivated just by scrambling the sequence of the CBEs. IGCR-1 regulates various aspects of IgH V to $DJ_H$ recombination, but most importantly in the context of our proposed antibody affinity maturation method, it suppresses the rearrangement of the $V_H 81X$ variable region gene segment which lies about 90 kb upstream. Thus, when IGCR1 is deleted, or just when the IGCR-1 CBEs are mutated, $V_H 81X$ is used in most $V_H$ to $DJ_H$ rearrangements on the mutated allele, despite the integrity of the full IgH locus other than the IGCR1/CBE mutations. Therefore, in ongoing experiments, we have deleted IGCR-1 in test ES cells in which $V_H 81X$ is replaced with human $IGV_H1\text{-}2^*02$. Because $IGV_H1\text{-}2^*02$ does not appear to be subject to appreciable negative selection during development, as suggested by the large fraction (70%) of productive $IGV_H1\text{-}2^*02$ rearrangement among mature B cells, we predict that the RDBC chimeras from ES cells in which human $IGV_H1\text{-}2^*02$ replaces $V_H 81X$ and IGCR-1 is inactivated will have peripheral B cells in which the human $IGV_H1\text{-}2^*02$ gene segment will be used to generate the majority of the peripheral B cell repertoire. If we make such ES cell homozygous by any of several methods commonly used on our lab or if we inactivate the second IgH allele (for example by deleting the 1 kb $J_H$ region or even by inactivating IGCR-1 so that only the counter-selected $V_H 81X$ is rearranged on it), we predict that nearly all B cells will use the $IGV_H1\text{-}2^*02$ for functional $V_H DJ_H$ rearrangements to generate the IgH chain of their BCR.

To establish an optimally efficient system for rapidly generating increased affinity variants of any desired human monoclonal antibody with known specificity, and to also provide a system to test immunization strategies to select for particular binding specificities from a desired $V_H DJ_H$ (and $V_L J_L$) rearrangement (for example, intermediates of highly mutated broadly neutralizing, anti-HIV antibodies), we performed the following additional modifications to the test ES cells to be used for RDBC:

We introduced a modification of the $V_H 81X$ locus to allow rapid and efficient gene targeted replacement with any desired human $V_H$ segment or human $V_H$ segment cassette. During our replacement of the $V_H 81X$ with the human $IGV_H1\text{-}2^*02$, we have inserted an I-SceI meganuclease site immediately downstream of $IGV_H1\text{-}2^*02$ to allow introduction of a DNA double strand break (DSB) at this target site by expression of the I-SceI endonuclease. Introduction of DSBs during gene targeting during future $V_H$ replacement experiments would be expected to greatly increase targeting efficiency. Likewise, the nascent Cas9/CRISPR technology can also be utilized for the same purpose (16). Alternatively, high targeting efficiency could also be achieved by introducing a recombination mediated cassette exchange system (17). This general approach allows us to rapidly modify test ES cells lacking IGCR-1 function so that they will have any desired human $V_H$ gene segment in place of $V_H 81X$. In RDBC chimeras made from these ES cells, the inserted human VH would rearrange at very high levels and dominate the repertoire of peripheral B cells.

We also modified the test ES cells to replace the mouse $J_H$ locus with a similarly highly targetable sequence (for example, with a Cas9/CRISPR target site) which could be replaced with a human D and $J_H$ cassette or a cassette with an assembled human $DJ_H$ which will serve as substrates for human $V_H$ to $DJ_H$ recombination events. In such kind of cells, the D and $J_H$ or $DJ_H$ could represent sequences used in $V_H DJ_H$ rearrangements of interest and could be modified in different ways, for example to alter CDR3 length or to introduce potential SHM targeting motifs to increase the efficiency of SHM.

The approaches outlined above were designed to incorporate the human V, D, J gene segments through de novo V(D)J recombination during B cell maturation in mice. The advantage of this approach is that V(D)J recombination can vastly expand the range of antigen binding specificities via introduction of CDR3 junctional diversity. However, this approach may not be optimal when a defined CDR3 is needed for antibody function. For example, to develop vaccination strategies to fully mature intermediates of anti-HIV broadly neutralizing antibodies (BnAbs) in mice, V(D)J exons encoding the maturation intermediates must be expressed in B cells (18); such rearranged V(D)J exons sometimes contain unusual CDR3 regions that might have been generated in part during affinity maturation as opposed to during V(D)J recombination. On the other hand, expressing a rearranged V(D)J exon that has already undergone SHM in the periphery is sometimes problematic because the rearranged V(D)J exon may exhibit reactivity toward self antigens and, therefore, cause deletion of the corresponding B cells during maturation in bone marrow (19). This problem has previously hampered expression of fully matured V(D)J exons encoding anti-HIV BnAbs in mice.

To circumvent this problem, we used a V(D)J exon inversion and/or deletion system to express a desired V(D)J "passenger" exon in specifically mature B cells. For inversional activation of a desired passenger V(D)J exon, we will introduce a LoxP site downstream of the $J_H$ locus in the test ES cell line. We will then insert cassettes in place of $V_H 81X$ in the test ES cells which contain an inverted LoxP site (relative to $J_H$ loxP site) upstream of a desired inverted human passenger $V_H DJ_H$ exon which, in turn, is upstream of a normally oriented $V_H$ segment (e.g. $IGV_H1\text{-}2^*02$) that is not selected against when incorporated into primary $V_H(D)J_H$ rearrangements. The downstream $V_H$ segment in the cassette would be developmentally rearranged and promote developmental progression and subsequently the upstream inverted passenger $V_H DJ_H$ exon could be inverted by Cre-LoP mediated inversional recombination in peripheral B cells, for example through expression of cre recombinase under the control of CD21 promoter (20). Analogous inversional strategies were used to change BCR antigen binding specificity in memory B cells (21). Mice with B cells expressing the inverted V(D)J exon could then be immunized to select for affinity matured variants of the peripherally activated V(D)J segments. The same general approach could be used to activate expression of a desired passenger V(D)J exon in mature B cells via a deletional approach in which the upstream cassette V(D)J exon is in the same orientation as the downstream $V_H$ in cassette and the LoxP sites are oriented to delete the downstream V(D)J exon in the periphery and thereby activate the upstream passenger V(D)J exon.

We also tested ES cells that were further modified by introducing relevant human rearranged $V_L J_L$ into the mouse IgL locus so that the evolution of a particular antibody specificity can be carried out in the context of both the appropriate human IgH and IgL. For example, some anti-HIV broadly neutralizing antibodies are encoded by affinity-matured forms of human IGHV1-2*02 and IGκV1 alleles (18). Expression of the affinity-matured form of IGκV1 may facilitate the affinity maturation of the IGHV1-2 allele in response to immunization with the HIV antigen.

We further tested whether ES cells could be modified to introduce any additional known or yet to be identified mutations that could activate, inactivate, or modify genes that, in a lymphocyte-intrinsic fashion, could lead to increased GC antibody maturation responses. Examples of such mutations have been reported in the literature (22, 23)

In summary, we used the RDBC chimeras derived from the various ES cell lines for immunization protocols that can further improve therapeutic antibodies for clinical application. Appropriately designed RDBC chimeras also can be used to evaluate the efficacy of vaccine candidates and immunization protocols on affinity maturation. As described earlier, current immunization and phage display approaches have generated effective therapeutic antibodies against target antigens, but many such antibodies may not always meet the requirements for specificity and affinity required for intended clinical applications, or even if they do they could be potentially further improved in the affinity/specificity.

To improve such antibodies, we can use their IgH V segments to replace $V_H 81X$ in our system, in analogy to our experiments with IGHV1-2*02 replacement. In this approach, the IgH variable region will undergo V(D)J recombination, which will expand the diversity of CDR3 through the combination of different human $D_H$ and $J_H$ segments as well as the addition of junctional nucleotides.

A pre-assembled $DJ_H$ rearrangement corresponding to that used in the original antibody also can be used to drive further maturation pre-exiting antibody of known specificity. In this setting, the mouse contains predominantly B cells that express a modified version of the antigen binding IgH variable region but with vastly expanded range of CDR3's due to the addition of junctional nucleotides at the $V_H$-D joint. The junctional diversification of IgH CDR3 can potentially create more specific antigen-binding sites relative to that in the original antibody, and such antibodies can be selected out by immunizing the mouse with the target antigen. Subsequent to immunization, the Ig variable regions can undergo somatic hypermutation to further improve antigen-binding specificity.

Thus, in our system, an IgH V(D)J region already selected for binding a specific antigen will be further modified by V(D)J recombination and SHM. With proper antigenic selection, the combination of these two mechanisms results in tremendous improvements in antibody specificity and affinity.

In cases where a defined CDR3 is needed, the V(D)J exon inversion system can be used to express such rearranged V(D)J exon in mature B cell stage to avoid complications of counter selection against self-reactivity during early stages of B cell development. As outlined, the system can be modified to provide desired IgL chains to further direct antibody affinity maturation.

Finally, one can further optimize the methods by introducing mutations that enhance the antibody response in a lymphocyte specific fashion.

Our approach can be used to improve affinity and/or specificity of any therapeutic antibody. A major advantage of this approach, is that it can offer the ability to generate a cohort of mice for immunization that express any desired set of human variable region exons in a large fraction of peripheral B cells in less than 6 months from initial targeting to immunization.

As one example, below, we outline an additional application of the approach in the context of HIV vaccine development strategies. In addition to HIV vaccines, a broad-spectrum vaccine for influenza is needed to effectively control seasonal flu and to preempt pandemics caused by new influenza strains. BnAbs against influenza virus have also been identified, and similar to HIV BnAbs, the influenza BnAbs also appear to arise from particular human $V_H$ segments, for example IGHV1-69 (24). Thus, the approach outlined below for HIV vaccine development may be equally applicable to informing influenza or other vaccine development strategies.

Protection from HIV Infection by Broadly Neutralizing Antibodies (BnAbs)

As a proof-of-principle experiment and also to solve a clinically important but hitherto intractable problem, we propose use of our system to facilitate testing of approaches for development of HIV vaccine. An HIV vaccine is urgently needed to control the AIDS epidemic. So far, HIV vaccination has been based on the traditional approach of immunizing human subjects with various HIV antigens. The principal surface protein of HIV is gp120, which binds to CD4 on T cells and mediates viral entry. A major goal of HIV vaccine has been to induce antibody against gp120 in order to block infection. However, immunization with gp120 failed to protect human subjects against HIV infection in clinical trials. This failure is due to the diversity of HIV strains; immunization with gp120 from one viral strain induces neutralizing antibody against that particular HIV strain only, but is powerless against many divergent viral strains. One way out of this dilemma is to target antibodies toward a conserved part of gp120. The feasibility of this approach is supported by the recent identification of broadly neutralizing antibodies (BnAbs) against a wide spectrum of HIV strains among certain AIDS patients (3). The potency of anti-HIV BnAbs lies in their tight binding to gp120 CD4 binding site, which is critical for viral invasion into T cells (25). In light of this discovery, protection against HIV infection could potentially be accomplished with vaccines that are capable of eliciting BnAbs.

Based on bioinformatic analysis, the BnAb Ig genes from several AIDS patients appear to share a germline $V_H$ gene segment as their common ancestor, $IGV_H 1$-2*02. During evolution from the germline $IGV_H 1$-2*02 to that employed in anti-HIV BnAbs, the $IGV_H 1$-2*02 sequence accumulates as much as 30% mutations, presumably owing to extensive somatic hypermutation in response to chronic HIV infection or potentially due to acquisition of SHM targeting motifs during the affinity maturation process (3). These mutations are functionally important, as reversion of the mutations to the germline sequence abolishes the neutralization activity of BnAbs. Structural analyses of the BnAb/gp120 complex offered a plausible explanation as to why $IGV_H 1$-2*02 is a suitable precursor to BnAbs. The BnAb interacts with gp120 CD4 binding site primarily through the IgH variable region, and certain amino acid residues in $IGV_H 1$-2*02 establish critical contacts with the gp120 CD4 binding site. The interaction between $IGV_H 1$-2*02 and gp120 CD4 binding site is further augmented with extensive somatic hypermutations that remodel the IgH variable region into a structural mimic of CD4, the natural ligand of gp120 (18).

Based on this information, to induce BnAbs, the vaccine should activate B cell that expresses $IGV_H1$-2*02 as part of its B cell receptor, and the activated B cell may need to undergo very extensive somatic hypermutation to tailor antibody variable regions into a close fit for the gp120 CD4 binding site. Although conceptually simple, modeling this approach requires several reagents that have not been readily available.

First, although $IGV_H1$-2*02 is the precursor to BnAbs, gp120 interacts poorly with antibodies containing the germline $IGV_H1$-2*02, and a custom-designed antigen may be needed to trigger $IGV_H1$-2*02 expressing B cells.

Second, the path from $IGV_H1$-2*02 to BnAb involves extraordinary levels of somatic hypermutation; given the intrinsically random nature of the mutation process, the B cells need to be guided along the productive mutation pathway toward BnAbs. Based on bioinformatic analysis, the affinity maturation process appears to involve a series of intermediates with increasing binding affinity toward the gp120 CD4 binding site, and the directed evolution of affinity maturation could potentially be accomplished with antigens specific for the affinity maturation intermediates. Overall, the successful induction of BnAbs may entail multiple antigens: one that activates B cells expressing germline IGHV1-2*02 and ones that select for affinity maturation intermediates.

To realize the vaccination scheme outlined above, antigens could be designed through protein engineering as shown in a recent report of a rationally designed antigen that binds to antibodies containing the germline IGHV1-2*02 (26). However, the ability of such engineered antigens to activate relevant B cells in vivo needs to be evaluated in animal models. To fill this need, we have generated test ES cells to produce RDBC chimeras in which most B cells express IGHV1-2*02 or its affinity maturation intermediates. These mice can provide in vivo assays for vaccine candidates designed to activate the respective B cell populations.

One conventional method of expressing a particular Ig variable region is to integrate a preassembled (rearranged) V(D)J exon into the J region of the Ig locus. Taking advantage of allelic exclusion, which ensures monoallelic expression of Ig genes, the rearranged V(D)J exon inhibits V(D)J recombination at the endogenous Ig loci, and represents the sole functional Ig variable region for either IgH or IgL. For our purposes, the main problem with this approach is that the germline version of BnAb is not completely known, owing to uncertainties in CDR3, which includes the region from $V_HD_H$ joint and $D_HJ_H$ joint. In this region, it is hard to ascertain whether a particular nucleotide was inserted into the joints during V(D)J recombination or introduced by somatic hypermutation in the course of B cell activation. The issue is important because CDR3 provides a key interface between antibody and antigen, and $IGV_H1$-2*02 may exhibit distinct binding preferences in association with different CDR3's.

To address these uncertainties, we used the following strategy to express $IGV_H1$-2*02 in association with diverse CDR3's, as would normally be the case in human B cells. In this scheme, $IGV_H1$-2*02 are used to replace $V_H81X$ in IGCR-1 mutated ES cells as outlined above to ensure dominant rearrangement of $IGV_H1$-2*02 to inserted human $D_H$ and $J_H$ segments or pre-rearranged $DJ_H$ joins that mimic those in HIV BnABs. In combination with the addition of random nucleotides at the D to $J_H$ or $V_H$ to $DJ_H$ junctions, the process creates a family of $IGV_H1$-2*02 IgH variable regions with diverse CDR3's. If $IGV_H1$-2*02 is expressed under this situation, it will be paired with mouse IgL; given the structural similarity between human and mouse immunoglobulin, the human IgH variable region is expected to form functional antigen-binding sites in association with mouse IgL. However, to further approximate the human immune system, we can engineer the B cells to express an mature anti-HIV BnAB IgL as outlined above to potentially direct the affinity maturation evolution of the IgH chain as needed. Also, if particular affinity maturation intermediates are difficult to express due to counter-selection during early development, we can use the inversion or deletion system outlined above to express them only in mature B cells.

Test RDBC chimeras can then be immunized with candidate antigens. After immunization, the somatic hypermutation status of $IGV_H1$-2*02 Ig variable region can be analyzed. In parallel, the antibody affinity for gp120 CD4 binding site are measured to determine whether immunization promotes affinity maturation. We can also incorporate mutation intermediates into our system and assay candidate antigens for their ability to activate B cells in the intermediate stages of affinity maturation. In addition to $IGV_H1$-2*02, other human $V_H$ segments, for example $IGV_H1$-46 (27), also serve as precursors to different types of BnAbs, which recognize several HIV targets including the CD4 binding site, V1V2 region and the glycan of gp120 and the membrane proximal external region (MPER) of gp41 (28). Besides extensive SHM, some of these BnAbs feature unusually long IgH CDR3. Our system is able to generate mice for immunization testing in which peripheral B cells express human IgH variable region exons that recapitulate long CDR3's during V(D)J recombination to generate such unusual antibodies.

REFERENCES

The references cited herein and throughout the specification and examples are herein incorporated by reference in their entirety.

1. P. J. Carter, Nat. Rev. Immunol. 6, 343 (2006).
2. F. Klein et al., Nature 492, 118 (2012).
3. X. Wu et al., Science 329, 856 (2010).
4. C. H. Bassing et al., Cell 109, S45 (2002).
5. F. Matsuda, Molecular Biology of B cells, 1 (2004).
6. J. Chaudhuri et al., Adv. Immunol. 94, 157 (2007).
7. J. M. Di Noia, M. S. Neuberger, Annu. Rev. Biochem. 94, 157 (2007).
8. N. Lonberg, Nature Biotechnology 23, 1117 (2005).
9. J. Chen et al., Proc. Natl. Acad. Sci. USA 90, 4528 (1993).
10. R. Riblet, Molecular Biology of B cells, 19 (2004).
11. G. D. Yancopoulos et al., Nature 311, 727 (1984).
12. F. Melchers et al., Immunol. Rev. 175, 33 (2000).
13. B. A. Malynn et al., J. Exp. Med. 171, 843 (1990).
14. D. J. Decker et al., J. Immunol. 147, 1406 (1991).
15. C. Guo et al., Nature 447, 424 (2011).
16. F. Ran et al., Nat. Protoc. 8, 2281 (2013).
17. Turan et al., Gene 515, 1 (2013).
18. X. Wu et al., Science 333, 1593 (2011).
19. G. Yang et al., J. Exp. Med. 210, 241 (2013).
20. M. Kraus et al., Cell 117, 787 (2004).
21. M. Maruyama et al., Nature 407, 636 (2000).
22. L. Lu et al., Proc. Natl. Acad. Sci. USA. 105, 19420 (2008).
23. H. J. Kim et al., Nature 467, 328 (2010).
24. D. Lingwood et al., Nature 489, 566 (2012).
25. T. Zhou et al., Science 329, 811 (2010).

26. J. Jardine et al., Science 340, 711 (2013).
27. J. F. Scheid et al., Science 333, 1633 (2011).
28. D. R. Burton et al., Science 337, 183 (2012).

Example 2

As noted above, HIV vaccine field would benefit from better mouse models to test in vivo immunization strategies to elicit therapeutically effective anti-HIV broadly neutralizing antibodies (bNABs) (1). To address this need, described herein is a new and rapid approach, based on RAG-2 deficient blastocyst complementation (RDBC) method, to generate chimeric mice expressing in their B cells specific human antibodies of interest to the HIV vaccine field for use in vaccination studies. This mouse model will facilitate studies of the efficacy of immunogens to stimulate affinity maturation of precursor antibodies into BnAbs.

Described herein is the generation of such a mouse model that expresses the unmutated precursor of VRC01. The germline $V_H$ segment of VRC01 is IGHV1-2*02 (2). To express IGHV1-2*02 in mice, homology-mediated gene-targeting was used to substitute IGHV1-2*02 for mouse $V_H81X$ in mouse embryonic stem (ES) cells (FIG. 1A, step 1). Since $V_H81X$ is the most frequently utilized mouse $V_H$ segment for V(D)J recombination (3), it was postulated that IGHV1-2*02 would experience the same rearrangement preference when inserted in place of $V_H81X$. Mice that contain the IGHV1-2*02 replacement were generated. In these mice, approximately 4% of B cells harbored rearranged IGHV1-2*02 (FIGS. 2A and 2B). Given that the mouse IgH locus contains more than 100 $V_H$ segments, this result indicates that IGHV1-2*02 is indeed preferentially utilized for V(D)J recombination.

We modified the $V_H81X$ locus so that any human $V_H$ segment introduced into this locus will undergo efficient rearrangement and dominate the repertoire of mature B cells in peripheral lymphoid tissues.

We integrated human $DJ_H$ or $J_H$ segments of BnAbs into the mouse $J_H$ locus so that they can be joined to the human $V_H$ segments at $V_H81X$ locus. In addition, we proposed to modify the mouse $J_H$ locus to facilitate the introduction of other human $J_H$ segments into the locus in the future.

To express the human Ig light chain (IgL) of BnAbs by integrating a pre-rearranged version of the IgL variable region into the mouse Igk locus.

We tested whether certain mutations can accelerate the process of affinity maturation.

We used the system described herein to express affinity maturation intermediates of VRC01. These mice were used to show that sequential immunization of an unmutated ancestor or mutation intermediates can guide affinity maturation toward fully mature BnAbs.

Deletion of IGCRI Element.

IGCRI is a regulatory element in the intervening region between $V_H$ and Ds (5). Deletion of IGCRI accentuates the biased utilization of $V_H81X$ for V(D)J recombination (5). In light of this observation, IGCRI was deleted from the IgH allele into which IGHV1-2*02 was incorporated (FIG. 1A step 2). The IGHV1-2*02/IGCRID ES cells were injected into Rag2 deficient blastocysts to generate chimeric mice. Since Rag2 is essential for V(D)J recombination, B and T cells can only derive from the Rag2 sufficient ES clones, but not from the Rag2 deficient blastocysts (4). This RDBC method permits the evaluation of the impact of any genetic manipulation of ES cells on B and T cells in chimeric mice. The frequency of IGHV1-2*02 usage in mature B cells in the IGHV1-2*02/IGCRID chimeric mice was determined (FIGS. 2A and 2B). Based on hybridoma analysis, 59% of splenic B cells contained rearranged IGHV1-2*02. Thus, deletion of IGCRI increased usage of IGHV1-2*02 by 15-fold. Recombination joints involving IGHV1-2*02 were sequenced and it was found that 20% were productive (FIG. 2C). Without wishing to be bound by theory, non-productive IGHV1-2*02 rearrangements were presumably carried through B cell development by productive rearrangements of the other IgH allele.

Deletion of $J_H$ Region of the $IgH^b$ Allele.

To limit V(D)J recombination to the IgH allele containing IGHV1-2*02, the $J_H$ region of the other IgH allele was deleted. The ES cell used herein derives from an F1 hybrid between 129 and C57BL/6 mice. The IgH alleles of 129 and C57BL/6 mice belong to the $IgH^a$ and $IgH^b$ allotypes respectively; IGHV1-2*02 replacement and IGCRI deletion occurred on the $IgH^a$ allele. To inactivate the $IgH^b$ allele, the $J_H^b$ region was deleted (FIG. 1B, step 3) and the manipulated ES cells were used for RDBC. The frequency of IGHV1-2*02 usage among splenic B cells in IGHV1-2*02/IGCRID/$J_H^b$ RDBC mice was determined and it was found that 34% of the B cells contained IGHV1-2*02 rearrangements, all of which were productive (FIGS. 2A-2D). Thus, the IGHV1-2*02/IGCRID/$J_H^b$ ES clone can serve as an efficient platform to express any human $V_H$ segment in mouse models.

Incorporation of the Ig Light Chain (IgL) for the Unmutated Precursor of VRC01 into Mouse Jk Locus.

The signature of the IgL chain for the VRC01 family of BnAbs is a short 5-amino acid CDR L3 (6). As the chance of obtaining such short CDR L3 through de novo rearrangement is low, a pre-rearranged version of unmutated VRC01 IgL was integrated into the mouse $Jk^a$ locus (FIG. 1C, step 4). The ES clone (IGHV1-2*02/IGCRID/$J_H^b$DNRC01LC) was injected into Rag2 deficient blastocysts to generate chimeric mice.

Integration of Human $J_H2$ Segment into Mouse $J_H$ Locus.

The only conserved feature of CDR H3 for the VRC01 family is a W residue at position 100B (6), which can be provided by the human $J_H2$ segment. Because of high levels of mutation in VRC01 antibodies and the random nature of N-nucleotides, it is difficult to ascertain the authentic germline CDR H3 sequence, including the identity of the D segment. Therefore, only the human $J_H2$ segment was integrated into mouse $J_H^a$ locus; recombination of human $J_H2$ with mouse D segments will create diverse CDR H3's. Given the variable nature of CDR H3 of VRC01 family of antibodies (6), at least a fraction of the CDR H3 generated by this combination are compatible with the interaction of VRC01 with gp120. In addition, diverse CDR H3s permits the selection of antibodies that bind gp120, but do not cross-react with self-antigens and therefore will not be subject to developmental blocks via bone marrow tolerance mechanisms. A targeting construct was generated to replace the entire mouse $J_H1$-$J_H4$ region with human $J_H2$ (FIG. 1A, step 5). The targeting construct was introduced into the IGHV1-2*02/IGCRID/$J_H^b$DNRC01LC ES clone.

We also tested whether Qa-1 mutation could enhance germinal center reaction. Certain mutations in Qa-1 have been shown to lead to abnormally large germinal centers in mice (7). We explored the incorporation of such Qa-1 mutations into the presently described system to see if it would accelerate affinity maturation. However, we were unable to find additional benefits from the mutation as we found that the frequency of somatic hypermutation is comparable between Qa-1 and control mice (data not shown).

A mouse system for expressing the unmutated precursor of VRC01 antibody was constructed. To facilitate the incorporation of other human antibody genes into this system, an I-SceI cleavage site was introduced into the V$_H$81X locus and a target sequence for a guide RNA of Cas9 into the Jk□ locus; the targeting construct for integrating the human J$_H$2 into the J$_H$ locus can also integrate a target site for a guide RNA of Cas9. Introduction of double strand breaks at these loci by I-SceI or Cas9 can increase the efficiency of gene targeting. The modified ES clones can be used with the RDBC approach to efficiently generate cohorts of chimeric mice. Moreover, all of the RDBC chimeric mice so far transmit their genetic modifications into the germline.

Mouse Model Expressing Unmutated Precursor of VRC01.

Described herein is a mouse model expressing the unmutated precursor of VRC01 as well as mice that include the VRC01 Ig light chain and the human J$_H$2 segment. Also described herein are, e.g. ES cells, which incorporate the various affinity maturation intermediates of VRC01 (8).

Development of Conditional Expression System for BnAbs that are Subject to Negative Control by Tolerance Mechanisms in the Bone Marrow.

Some BnAbs are poly-reactive and can bind to self-antigens. As a result, B cells expressing these BnAbs in mice are subject to developmental blockage by tolerance mechanisms in bone marrow (9). To address this issue, described herein is a strategy to express BnAbs specifically in mature B cells, thereby circumventing tolerance mechanisms in the bone marrow. To achieve this goal, Ig variable region genes are expressed that encode non-self reactive antibodies in B cell precursors in bone marrow; these antibody genes are referred to herein as "driver V genes" (FIG. 3). The BnAb genes will be positioned upstream of the driver V genes and will not be expressed in bone marrow. When these B cells have become mature B cells in peripheral lymphoid tissues, the driver V gene will be deleted by flanking loxP sites by cre recombinase that is specifically expressed in mature B cell stage (CD21-cre, FIG. 3). As a result, the BnAb genes will replace the driver V gene and be expressed in mature B cells. This method can be used to express, e.g., BnAbs VRC26 (10) and DH270. An ES cell line was derived from CD21-cre transgenic mice; so that the conditional expression construct can be directly introduced into the CD21-cre ES cell line instead of relying on mouse breeding Conditional expression constructs for VRC26 and DH270 have been constructed and transfected into CD21-cre ES cells.

Optimization of BnAbs for Treating HIV Infection.

Described herein is the adaptation of the above-described system to improve BnAbs for AIDS therapy. For this application of the presently-described approach, the V$_H$ and DJ$_H$ segments of BnAbs are incorporated into the V$_H$81X and J$_H$ loci respectively (FIG. 4). When the V$_H$ and DJ$_H$ segments are joined via V(D)J recombination during B cell development, junctional diversity would greatly expand the range of CDR H3, essentially creating a library of related antibodies with subtle differences in antigen binding site. Immunization with target antigen would select out B cells expressing high affinity antibodies, which will be further optimized through somatic hypermutation. In some embodiments, the BnAbs can be DH270 or CH103 (11). The mature DH270 antibody contains relatively low levels of somatic hypermutation, potentially leaving more room for further optimization by additional rounds of affinity maturation. The mutation frequency of CH103 antibody is also lower than that reported for VRC01, and does not exhibit as broad a range of neutralization activity as some of the other BnAbs. For both DH270 and CH103, CDR H3 constitutes an important part of the interface with HIV envelope protein.

REFERENCES

1. J. R. Mascola, B. F. Haynes, *Immunological Reviews* 254, 225 (2013).
2. X. Wu et al., *Science* 329, 856 (2009).
3. G. D. Yancopoulos et al., *Nature* 311, 727 (1984).
4. J. Chen et al., *Proc. Natl. Acad. Sci. USA* 90, 4528 (1993).
5. C. Guo et al., *Nature* 447, 424 (2011).
6. A. P. West et al., *Proc. Natl. Acad. Sci. USA* 109, E2083 (2012).
7. H. J. Kim et al., *Nature* 467, 328 (2010).
8. X. Wu et al., *Science* 333, 1593 (2011).
9. Y. Chen et al., *Journal of immunology* 191, 1260 (2013).
10. N. A. Doria-Rose et al., *Nature* 509, 55 (2014).
11. H. Liao et al. *Nature* 496, 469 (2013).

We claim:

1. A cell comprising an engineered IgH locus in which the 3'-most $V_H$ segment of the IgH locus comprises a non-native $V_H$ segment sequence; and
the engineered IgH locus does not comprise a functional IGCR1 sequence within the nucleic acid sequence separating the 3' end of the 3'-most $V_H$ segment of the IgH locus and the 5' end of a $D_H$ segment of the IgH locus.

2. The cell of claim 1, wherein the non-native $V_H$ segment is a human $V_H$ segment.

3. The cell of claim 1, wherein the non-native $V_H$ segment is a human $V_H$ segment from a known antibody in need of improvement of affinity or specificity.

4. The cell of claim 3, wherein the human $V_H$ segment is IGHV1-2*02, IGVH1-46 or IGHV1-69.

5. The cell of claim 1, further comprising:
(a) a 3' recombinase site being located 3' of the one or more $J_H$ segments;
and a passenger cassette being located at the position of a deleted native 3'-most $V_H$ segment, the passenger cassette comprising, from 5' to 3':
a 5' recombinase site
an inverted passenger VDJ exon and/or a cassette targeting sequence; and
a maturation-compatible $V_H$ segment;
wherein the recombinase sites are inverted with respect to each other; or
(b) a 3' recombinase site being located 3' of the one or more $J_H$ segments;
and a passenger cassette being located at the position of a deleted native 3'-most $V_H$ segment, the passenger cassette comprising, from 5' to 3':
a 5' to 3'-oriented passenger VDJ exon and/or a cassette targeting sequence;
a 5' recombinase site; and
a maturation-compatible $V_H$ segment;
wherein the recombinase sites are in the same orientation.

6. The cell of claim 5, wherein the recombinase site is a LoxP site and the cell further comprises a locus encoding cre recombinase.

7. The cell of claim 6, wherein the locus encoding cre recombinase is under the control of a promoter which is not active in immature B cells and is active in peripheral B cells.

8. The cell of claim 7, wherein the promoter is the CD21 promoter.

9. A genetically engineered non-human mammal comprising the cell of claim 1.

10. A chimeric genetically engineered non-human mammal comprising two populations of cells,
a first population comprising cells which are V(D)J recombination-defective; and
a second population comprising cells of claim 1.

11. A method of making an optimized antibody from a known antibody, the method comprising the steps of:
injecting a mouse blastocyst with a cell of claim 1, wherein the cell is a mouse embryonic stem cell, and wherein the non-native $V_H$ segment comprises the $V_H$ segment of the known antibody;
implanting the mouse blastocyst into a female mouse under conditions suitable to allow maturation of the blastocyst into a genetically engineered mouse;
isolating
1) An optimized antibody comprising the non-native $V_H$ segment; or
2) a cell producing an optimized antibody comprising the non-native $V_H$ segment from the genetically engineered mouse.

12. A method of producing B lymphocytes comprising $V_H(D)J_H$ rearrangements with a VH segment from a known monoclonal antibody, the method comprising the steps of:
injecting engineered mouse embryonic stem cells which are cells according to claim 1 and wherein the non-native $V_H$ segment comprises the $V_H$ segment of the known monoclonal antibody, into a blastocyst of a mouse which is incapable of forming mature B cells, thereby creating a chimeric mouse that produces B lymphocytes comprising $V_H(D)J_H$ rearrangements comprising the $V_H$ segment from the known monoclonal antibody.

13. A method of identifying a candidate antigen as an antigen that activates a B cell population comprising a $V_H$ segment of interest, the method comprising:
immunizing a mammal of claim 9, engineered such that a majority of the mammal's peripheral B cells express the $V_H$ segment of interest, with the antigen;
measuring B cell activation in the mammal; and
identifying the candidate antigen as an activator of a B cell population comprising the $V_H$ segment of interest if the B cell activation in the mammal is increased relative to a reference level.

14. The cell of claim 1, wherein the engineered IgH locus comprises a non-functional IGCR1 sequence comprising mutated CBE sequences; the engineered IgH locus comprises a non-functional IGCR1 sequence in which CBE sequences of the IGCR1 sequence have been deleted; or the IGCR1 sequence has been deleted from the engineered IgH locus.

15. The cell of claim 1, wherein the cell is a murine cell.

16. The cell of claim 15, wherein the cell is a murine stem cell or murine embryonic stem cell.

17. The cell of claim 1, wherein the cell is a stem cell or embryonic stem cell.

18. The cell of claim 1, wherein the IgH locus further comprises at least one of the following:
    one or more non-native $D_H$ segments;
    one native $D_H$ segment;
    one or more non-native $J_H$ segments, the
    a human $J_H2$ $J_H$ segment
    one native $J_H$ segment;
    a murine IgH locus sequence;
    a human IgH locus sequence; and
    a humanized IgH locus sequence.

19. The cell of claim 1, wherein the $J_H$ locus has been replaced by human D and $J_H$ cassette or a cassette with an assembled human $DJ_H$.

20. The cell of claim 1, wherein the cell is heterozygous for the engineered IgH locus of claim 1 and the other IgH locus has been engineered to be inactive, wherein the cell will express an IgH chain only from the engineered IgH locus of claim 1.

21. The cell of claim 1, further comprising at least one of the following:
    an IgL locus with human sequence;
    a humanized IgL locus;
    a human IgL locus;
    an IgL locus with one $V_L$ segment;
    an IgL locus with one $J_L$ segment;
    a human rearranged $V_LJ_L$ at the IgL kappa or lambda locus;
    a human rearranged $V_LJ_L$ at the murine IgL kappa or lambda locus; and
    an IgL locus encoding IGκV1 or VRC01 IgL.

22. The cell of claim 1, further comprising a mutation capable of activating, inactivating or modifying genes leading to increased GC antibody maturation responses.

* * * * *

SEQUENCE LISTING

```
<160> NUMBER OF SEQ ID NOS: 2

<210> SEQ ID NO 1
<211> LENGTH: 317
<212> TYPE: DNA
<213> ORGANISM: Homo sapiens

<400> SEQUENCE: 1
aggtgaagaa ggccggggcc tcagtgaagg tctcctgcga ggcttctgga tacagtttca      60
ccggccacta tatacactgg gtgcgacagg cccctggtca agggcttgag tggatgggat     120
ggatcaagcc ttccagtggt gacacaaact ttgcagagaa gtttcagggc agggtcacct     180
tgaccaggga cacgtccaag agcacagcct acatggagtt gatcaggctg agacctgacg     240
acacggccgt gtattactgt gcgaggatac acggatacag taatggctgg ttccctcttg     300
atgcttttga tatctgg                                                    317

<210> SEQ ID NO 2
<211> LENGTH: 328
```

```
<212> TYPE: DNA
<213> ORGANISM: Homo sapiens

<400> SEQUENCE: 2
caggtgcagt tggtgcagtc tggggctgag gtgaagaggc ctggggcctc agtgaaggtt      60
tcctgcaaga catctggata caccttcacc agctattctt tacactgggt gcgacaggcc     120
cctggacaag gacttgagtg gatgggaata atcaaccta gtgatggtag cacaaattac      180
gcacagaagt tccagggcag agtcattatg accagggaca cgtccacgag cacagtctac     240
atggagctga ggagcctgag atctgaggac acggccttt attactgtgc gagagcctat      300
aggacctatg atccttttga tatgtggg                                         328
```